United States Patent

Frei et al.

Patent Number: 5,840,911
Date of Patent: Nov. 24, 1998

[54] IMIDAZOLE DERIVATIVES, THEIR PREPARATION AND THEIR USE AS S-ADENOSYLMETHIONINE DECARBOXYLASE (=SAMDC) INHIBITORS

[75] Inventors: Jörg Frei, Hölstein; Jaroslav Stanek, Arlesheim, both of Switzerland

[73] Assignee: Novartis AG, Basle, Switzerland

[21] Appl. No.: 875,299

[22] PCT Filed: Jan. 15, 1996

[86] PCT No.: PCT/EP96/00143

§ 371 Date: Jul. 23, 1997

§ 102(e) Date: Jul. 23, 1997

[87] PCT Pub. No.: WO96/22979

PCT Pub. Date: Aug. 1, 1996

[30] Foreign Application Priority Data

Jan. 26, 1995 [CH] Switzerland ................ 215/95

[51] Int. Cl.$^6$ ............... C07D 233/88; C07D 233/46; A61K 31/415
[52] U.S. Cl. ............... 548/326.5; 548/331.5; 548/332.5; 514/398
[58] Field of Search ............... 548/326.5, 331.5, 548/332.5; 514/398

[56] References Cited

U.S. PATENT DOCUMENTS 4,659,720  4/1987  Chabala et al. .................. 514/313

FOREIGN PATENT DOCUMENTS 327919  8/1989  European Pat. Off. ......... A61K 7/22

OTHER PUBLICATIONS

Harmon R.E. et al., Journal of Pharmaceutical Sciences, Cytotoxic Activity of Imidazole Derivatives vol. 59, No. 5, p. 724, May 1970.
Stanek J. et al., Journal of Medicinal Chemistry, vol. 36, No. 15, pp. 2168–2171, Jul. 23, 1993.
Stanek J. et al., Journal of Medicinal Chemistry, vol. 36, No. 1, pp. 46–54, Jan. 8, 1993.
J.Chem. Soc., Perkin Trans. 1(11), 3085–9 (1990).
Acta Pharm. Turcica XXIX, 51 (1987) corresponds to Chem. Abstr. 108:68752a(1988).
Farmacao, Ed. Sci. 42(6), 449–56 (1987) corresponds to Chem.Abstr. 107:93355k (1987).
Res. Discl. 162, 73–75 (1977).
English version of Khim. Geterotsikl. Soedin 6, 846–850 (1974), corresponding to Chem. Abstr. 81: 120563e (1974).
J. Heterocycl. Chem. 11(3), 327–9 (1974).
English Version of Khim. Geterotsikl. Soedin 9, 1190–93 (1973), corresponding to Chem. Abstr. 79: 146458h (1973).
Chem. Ber. 100, 3418–26 (1967), corresponding to Chem. Abstr. 67:108595v (1967).
English Version of Khim. Geterotsikl. Soedin 19(1), 82–87 (1983) corresponding to Chem. Abstr. 111: 153764n (1989).
English Version of Khim. Geterotsikl. Soedin 2, 242–5 (1982), corresponding to Chem. Abstr. 97: 72286y (1982).
Cancer Res., 54, 3210–17 (1994).
Noville et al., (CA 127:346394, WO 9736875), 1997.

Primary Examiner—S. Mark Clardy
Assistant Examiner—Sabiha N. Qazi
Attorney, Agent, or Firm—Joseph J. Borovian

[57] ABSTRACT

Described are compounds of formula I

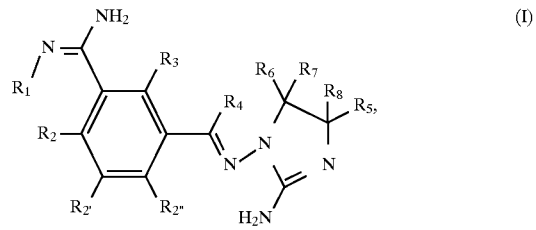

wherein
  $R_1$ is hydrogen or hydroxy;
  $R_2$, $R_2'$ and $R_2''$ are each independently of the others hydrogen or a substituent other than hydrogen;
either
  $R_3$ is hydrogen or a substituent other than hydrogen and
  $R_4$ is hydrogen or lower alkyl,
or
  $R_3$ and $R_4$ together form a divalent radical of the formula $-(CH_2)_n-$ wherein n is 2 or 3;
  $R_5$ and $R_6$ are each independently of the other hydrogen, alkyl or aryl; and
  either $R_7$ and $R_8$ are each hydrogen, or $R_7$ and $R_8$ together form a bond; tautomers thereof, provided that at least one tautomerisable group is present; and salts thereof.

The compounds inhibit the enzyme S-adenosylmethionine decarboxylase and are suitable, for example, for the treatment of tumours and protozoal infections.

18 Claims, No Drawings

5,840,911

IMIDAZOLE DERIVATIVES, THEIR PREPARATION AND THEIR USE AS S-ADENOSYLMETHIONINE DECARBOXYLASE (=SAMDC) INHIBITORS

This application has been filed under 35 USC 371 as a National Stage application of PCT/EP 96/00143, filed Jan. 15, 1996.

BRIEF DESCRIPTION OF THE INVENTION

The invention relates to novel imidazole derivatives, to tautomers thereof and/or to salts thereof, to a process for the preparation of those compounds, to pharmaceutical compositions comprising those compounds, and to a) those compounds for use in, or b) the use of those compounds for, the therapeutic treatment of the human or animal body; and/or to the use of those compounds in the preparation of pharmaceutical compositions.

BACKGROUND OF THE INVENTION

It is known that inhibition of S-adenosylmethionine decarboxylase can be used for therapeutic purposes. Surprisingly, a novel class of compounds having valuable pharmacological properties has now been found.

COMPLETE DESCRIPTION OF THE INVENTION

An imidazole derivative according to the invention is especially a compound of formula I wherein $R_1$ is hydrogen or hydroxy;

$R_2$, $R_2'$ and $R_2''$ are each independently of the others hydrogen or a substituent other than hydrogen;

either $R_3$ is hydrogen or a substituent other than hydrogen and $R_4$ is hydrogen or lower alkyl, or $R_3$ and $R_4$ together form a divalent radical of the formula —(CH$_2$)$_n$— wherein n is 2 or 3;

$R_5$ and $R_6$ are each independently of the other hydrogen, alkyl or aryl; and either $R_7$ and $R_8$ are each hydrogen, or $R_7$ and $R_8$ together form a bond; a tautomer thereof, provided that at least one tautomerisable group is present; or a salt thereof.

Within the scope of the present Application, the general terms used hereinbefore and hereinafter have preferably the following meanings (unless indicated otherwise):

The term "lower" denotes a radical having up to and including a maximum of 7 carbon atoms, preferably up to and including a maximum of 4 carbon atoms.

Lower alkyl is, for example, n-propyl, isopropyl, n-butyl, isobutyl, sec-butyl, tert-butyl, n-pentyl, neopentyl, n-hexyl or n-heptyl, or, preferably, ethyl or, especially, methyl.

A substituent other than hydrogen is especially lower alkyl, halo-lower alkyl having one or more, preferably up to three, halogen atoms, cycloalkyl, aryl-lower alkyl, hydroxy, lower alkoxy, aryl-lower alkoxy, aryloxy, acyloxy, such as lower alkanoyloxy or arylcarbonyl-oxy, halogen, amino, N-lower alkylamino, N,N-di(lower alkyl)amino, acylamino, such as lower alkanoylamino or arylcarbonylamino, nitro, lower alkanoyl, arylcarbonyl, carboxy, lower alkoxycarbonyl, aryl-lower alkoxycarbonyl, such as 1-aryl-lower alkoxycarbonyl, for example benzyloxycarbonyl, carbamoyl (—CONH$_2$), N-lower alkylcarbamoyl, N,N-di(lower alkyl)carbamoyl, N-arylcarbamoyl, cyano, mercapto, lower alkylthio, lower alkanesulfonyl, sulfamoyl (—SO$_2$NH$_2$), N-lower alkylsulfamoyl or N,N-di(lower alkyl)sulfamoyl.

Halo-lower alkyl is especially mono-, di- or tri-(halo)-lower alkyl, such as trifluoromethyl.

Halogen is, for example, iodine or, preferably, bromine or, especially, fluorine or chlorine.

Cycloalkyl is preferably C$_3$–C$_8$cycloalkyl (having from 3 to 8 ring carbon atoms) and especially C$_5$–C$_6$cycloalkyl (having 5 or 6 ring carbon atoms), it being possible for cycloalkyl to be unsubstituted or substituted by lower alkyl.

Aryl is preferably an aromatic ring system having from 6 to 12 ring carbon atoms that is unsubstituted or substituted by one or more substituents of any kind selected independently of one another, and is bi- or, preferably, mono-cyclic; especially unsubstituted or substituted phenyl or naphthyl, such as 1- or 2-naphthyl; suitable substituents being preferably one or more, especially from one to three, more especially one or two, radicals selected independently of one another from the group consisting of lower alkyl, phenyl, naphthyl, such as 1- or 2-naphthyl, lower alkoxy, hydroxy, lower alkanoyloxy, nitro, amino, halogen, halo-lower alkyl, such as trifluoromethyl, carboxy, lower alkoxycarbonyl, carbamoyl, N-lower alkylcarbamoyl, N,N-di(lower alkyl)carbamoyl, cyano, lower alkanoyl, phenyl- or naphthyl-carbonyl, lower alkanesulfonyl, sulfamoyl, N-lower alkylsulfamoyl and N,N-di-lower alkylsulfamoyl. Aryl is especially 1- or 2-naphthyl; or phenyl that is unsubstituted or substituted by one or two radicals selected independently of one another from halogen, such as fluorine or chlorine (in each case especially in the p-position), lower alkyl, such as methyl or tert-butyl (in each case especially in the p-position), lower alkoxy, such as methoxy, and phenyl.

Aryl-lower alkyl preferably contains an aryl radical as defined above and is preferably phenyl-lower alkyl and, especially, benzyl.

Aryl-lower alkoxy preferably contains an aryl radical as defined above and is especially phenyl-lower alkoxy, such as benzyloxy.

Lower alkanoyl is especially foiinyl or, more especially, acetyl, propionyl or pivaloyl.

Lower alkanoyloxy is especially acetoxy, propionyloxy or pivaloyloxy.

Arylcarbonyl preferably contains an aryl radical as defined above and is, for example, benzoyl or 1- or 2-naphthoyl, each of which is unsubstituted or substituted by lower alkyl, lower alkoxy, hydroxy, halogen or by halo-lower alkyl, such as trifluoromethyl.

Lower alkanesulfonyl (lower alkyl—SO$_2$—) is preferably methane- or ethane-sulfonyl.

Alkyl is a hydrocarbon radical having preferably up to a maximum of 20 carbon atoms that is unbranched or has one or more branches, such as dodecyl, for example 1-(n-dodecyl), decyl, for example 1-(n-decyl), nonyl, for example 1-(n-nonyl), octyl, for example 1-(n-octyl), or, preferably, lower alkyl, such as, especially, methyl or, more especially, ethyl.

While the other radicals have the meanings given at each of the definition levels mentioned hereinbefore and hereinafter (generally defined compounds of formula I and preferred compounds of formula I), the following compounds are especially preferred:

a) compounds of formula I wherein RI is hydrogen are preferred to those wherein $R_1$ is hydroxy;

b) when $R_7$ and $R_8$ are each hydrogen, in preferred compounds of formula I $R_5$ and $R_6$ are likewise each hydrogen;

c) compounds of formula I wherein $R_3$ and $R_4$ together are —$(CH_2)_3$— or, especially, —$(CH_2)_2$— are preferred to those wherein $R_3$ is hydrogen or a substituent other than hydrogen and $R_4$ is hydrogen or lower alkyl.

When tautomerisable groups are present in the compounds of formula I, it is possible (for example depending upon the solvent, pH value or aggregate state) for compounds of formula I (and some precursors thereof) to be in the form of tautomers. For example, in compounds of formula I wherein $R_7$ and Rs are each hydrogen and the other radicals are as defined, the 4,5-dihydroimidazolyl radical may be in the following tautomeric forms:

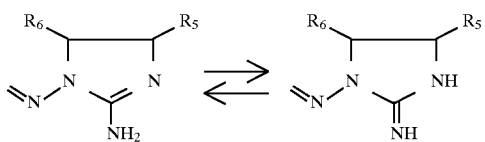

The person skilled in the art is familiar with the occurrence of such tautomers and of similar tautomers and can therefore easily infer the corresponding compounds and tautomers. The present invention relates also to such tautomers.

If cis/trans-isomerismn is possible and/or centres of asymmetry are present, compounds of formula I can be in the form of isomers or mixtures of isomers, for example in the form of mixtures of diastereoisomers, enantiomeric mixtures or pure isomers.

On account of their basic properties, salts of compounds of formula I are especially acid addition salts and, where one or more acid groups (such as —COOH) are present, also internal salts; mixed salts are also possible.

Salts are especially the pharmaceutically acceptable, that is to say non-toxic, salts of compounds of formula I, that is to say especially the corresponding acid addition salts with acid anions that are toxicologically tolerable (at the dose in question).

Such salts are formed, for example, by compounds of formula I with inorganic acids, for example hydrohalic acids, such as hydrochloric acid or hydrobromic acid, sulfuric acid or phosphoric acid, or with organic carboxylic, sulfonic, sulfo or phosphonic acids or N-substituted sulfamic acids, for example acetic acid, propionic acid, glycolic acid, succinic acid, maleic acid, hydroxymaleic acid, methylmaleic acid, fumaric acid, lactic acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, also with amino acids, such as the 20 a-amino acids involved in the synthesis of proteins in nature, for example glutamic acid or aspartic acid, and with methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acidic organic compounds, such as ascorbic acid. Carbonates or hydrogen carbonates are also possible.

The mixed salts include, for example, salts of compounds of formula I with di- or trivalent acids that have acidic radicals with different dissociation constants, such as citric acid or phosphoric acid, one or two protons of those acids, for example, being replaced by cations, such as alkali metal cations, for example $Na^+$ or $K^+$, so that the corresponding salts contain, in addition to the compound of formula I and the corresponding acid anions, also the corresponding cations.

Internal salts also may be in the form of mixed salts.

The terms "compounds" and "salts" expressly include also individual compounds or individual salts.

For isolation or purification it is also possible to use pharmaceutically unacceptable salts, for example picrates or perchlorates. Only the pharmaceutically acceptable, non-toxic salts are used therapeutically, and those salts are therefore preferred.

The compounds according to the invention have valuable, especially pharmacologically useful, properties. In particular, they have a pronounced, specific inhibitory action on the enzyme S-adenosylmethionine decarboxylase (SAMDC). SAMDC, as a key enzyme, plays an important role in polyamine synthesis, which takes place in virtually all mammalian cells, including human cells. SAMDC regulates the concentration of polyamines in the cell. Inhibition of the enzyme SAMDC results in a reduction in the polyamine concentration. Since a reduction in the polyamine concentration causes inhibition of cell growth, it is possible by administering SAMDC-inhibiting substances to inhibit the growth of both eukaryotic and prokaryotic cells and even to kill cells or inhibit the onset of cell differentiation. For example, it is possible to control tumors, for example in models, such as tumors produced by syngenic transplantation of tumor cells. Syngenic transplantation means transplantation within a strain of individuals that are genetically virtually identical.

Inhibition of the enzyme SAMDC can be demonstrated by conventional methods (for example by the method of H. G. Williams-Ashmann and A. Schenone, see Biochem. Biophys. Res. Communs. 46, 288 (1972), or preferably by the method of A. E. Pegg and H. S. Pösö, see Methods Enzymol. 94, 234–239 (1983)). The compounds of the invention have $IC_{50}$ values in the range of from $10^{-9}$ to $10^{-4}$M, especially from $2 \times 10^{-9}$ to $10^{-7}$M.

A further advantage of the compounds according to the invention is that they inhibit diamine oxidase only to a small extent as compared with their pronounced inhibitory action on SAMDC and are well tolerated. Inhibition of diamine oxidase is disadvantageous since it can lead to the accumulation of putrescine and hence to indirect activation of SAMDC (see J. Jaenne and D. R. Morris, Biochem. J. 218, 974 (1984)). The low degree of diamine oxidase inhibition can be determined by known methods (see, for example, P. Seppänen, L. Alhonen-Hongistu, K. Käpyaho and J. Jänne, Methods Enzymol. 94, 247–253 (1983)).

As polyamine antimetabolites, the compounds of formula I have antiproliferative properties which can be demonstrated, for example, by identifying the inhibitory action on the growth of human T24 bladder cell carcinomas. This is demonstrated by incubating the cells in "Eagle's Minimal Essential Medium" (see Eagle, H., Science 130, c1432–1437 (1959)), to which 5% (v/v) fetal calf serum is added, in a humidified incubator at 37° C. and 5% by volume $CO_2$ in the air. The carcinoma cells (1000–1500; ATCC HB 4) are transferred to 96-well microtitre plates and are incubated overnight under the said conditions. The test compound is added in serial dilutions on day 1. The plates are incubated under the said conditions for 5 days. During that period, control cultures undergo at least 4 cell divisions. After the incubation, the cells are fixed with 3.3% (weight/volume=w/v) aqueous glutaraldehyde solution, washed with water and stained with 0.05% (w/v) aqueous methylene blue solution. After washing, the dye is eluted with 3% (w/v) aqueous hydrochloric acid. The optical density (OD) per well, which is directly proportional to the number of cells, is then measured by means of a photometer (Titertek multiskan) at 665 nm. The $IC_{50}$ values are calculated by means of a computer system using the formula $$\frac{OD_{665}(\text{test}) - OD_{665}(\text{start})}{OD_{665}(\text{control}) - OD_{665}(\text{start})} \times 100$$

The $IC_{50}$ value is defined as the concentration of active ingredient at which the number of cells per well at the end of the incubation period is only 50% of the number of cells in the control cultures.

For compounds of formula I, $IC_{50}$ values in the range of from $10^{-4}$ to $5 \times 10^{-7}$ M, especially in the range of from $10^{-5}$ to $10^{-6}$ M, are obtained.

The tolerability and anti-tumor activity of the compounds of formula I in vivo can be demonstrated by known methods, for example using the method of U. Regenass, H. Mett, J. Stanek, M. Müller, D. Kramer and C. W. Porter (see Cancer Res. 54, 3210–3217 (1994)). Briefly, the procedure is as follows: To determine the maximum tolerable dose (MTD), the compounds according to the invention (for example dissolved in distilled water/0.9% NaCl) are injected i.p. into three mice per group. The dose is increased until the first animals die within a period of 10 days. To determine the anti-tumor activity, for example, small pieces of human T-24 bladder carcinoma cells (ATCC HTB 4) are cultured and transplanted as xenogenic transplants ("xenografts") into female BALB/c nude mice (Bomholtgarden, Copenhagen, Denmark). The anti-tumor treatment using compounds of formula I is started after at least three successive transplants. Tumor fragments weighing approximately 25 mg are transplanted into the left flank of the mouse (n=6 per group). Treatment is started as soon as the tumors have an average tumor volume of from 150 to 200 mm³. The growth of the tumors is determined twice weekly by measuring mutually perpendicular tumor diameters. The tumor volumes are determined in the manner described by U. Regenass, H. Mett, J. Stanek, M. Müller, D. Kramer and C. W. Porter (see Cancer Res. 54 3210–3217 (1994)) and are given as relative tumor size (i.e. increase in tumor volume relative to the tumor volume at the beginning of treatment) in T/C % (percent treated/control). The test compounds are dissolved in distilled water and diluted with 3 volumes of 0.9% (w/v) NaCl in water.

Values found for MTD are especially in the region of more than 200 mg/kg p.o. for example more than 500 mg/kg p.o.; or more than 50 mg/kg i.p., for example approximately 125 mg/kg i.p.. In the determination of the activity against tumors, dose-dependent inhibition of tumor growth on administration of compounds of formula I is found; in particular, in the case of p.o. administration marked reductions in tumor growth are found at a dose of as little as approximately 5 mg/kg, and in the case of i.p. administration very marked reductions in tumor growth are found at the lowest dose used (3.13 mg/kg), with preferred T/C values of less than 60%.

It is also possible to demonstrate the effectiveness of the compounds of formula I against trypanosomes using test systems known per se (see, for example, Brun, R. and Kunz, C., Acta Tropica 46 361–368 (1989)).

The compounds also exhibit good to very good plasma levels when administered p.o. (for example to mice).

When partitioned between octanol and water (log P determination), the compounds of formula I exhibit good lipophilicity.

Accordingly, the compounds of formula I can be used, for example, in the treatment of benign and malignant tumors. They are able to bring about the regression of tumors and also to prevent the spread of tumor cells and the growth of micrometastases. Moreover, they are beneficial, for example, in the treatment of protozoal infections, such as trypanosomiasis, malaria, or pulmonary inflammation caused by *Pneumocystis carinii*.

The corresponding diseases, especially tumor diseases, in warm-blooded animals, especially in mammalian domestic animals and in humans, can be treated.

As selective SAMDC inhibitors, the compounds of formula I can be used either on their own or in combination with other substances having pharmacological activity, for example in combination with (a) inhibitors of other enzymes of polyamine biosynthesis, for example ornithine decarboxylase inhibitors, (b) inhibitors of protein kinase C, (c) inhibitors of tyrosine protein kinase, (d) cytokines, (e) negative growth regulators, (f) aromatase inhibitors, (g) anti-oestrogens or (h) conventional cytostatic or also cytotoxic active ingredients.

Preference is given to a compound of formula I wherein $R_1$ is hydroxy or, especially, hydrogen; the radicals $R_2$, $R_2'$ and $R_2''$ are each independently of the others hydrogen or a substituent selected from lower alkyl, halo-lower alkyl having one or more, preferably up to three, halogen atoms, such as trifluoromethyl, $C_3$–$C_8$cycloalkyl, phenyl-lower alkyl, hydroxy, lower alkoxy, phenyl-lower alkoxy, phenyloxy, lower alkanoyloxy or benzoyloxy, halogen, amino, N-lower alkylamino, N,N-di(lower alkyl)amino, lower alkanoylamino, benzoylamino, nitro, lower alkanoyl, benzoyl, carboxy, lower alkoxycarbonyl, 1-phenyl-lower alkoxycarbonyl, for example benzyloxycarbonyl, carbamoyl, N-lower alkylcarbamoyl, N,N-di(lower alkyl) carbamoyl, N-phenylcarbamoyl, cyano, mercapto, lower alkylthio, lower alkanesulfonyl, sulfamoyl, N-lower alkylsulfamoyl and N,N-di-(lower alkyl)sulfamoyl;

either
    $R_3$ is hydrogen and
    $R_4$ is hydrogen or lower alkyl
or
    $R_3$ and $R_4$ together form a divalent radical of the formula —(CH$_2$)n— wherein n is 2 or 3;

$R_5$ and $R_6$ are each independently of the other hydrogen, lower alkyl, such as methyl or ethyl; or phenyl or naphthyl each of which is unsubstituted or mono- to tri-substituted, especially mono- or di-substituted, such as 1- or 2-naphthyl, wherein the substituents are selected independently of one another from the group consisting of lower alkyl, phenyl, naphthyl, lower alkoxy, hydroxy, lower alkanoyloxy, nitro, amino, halogen, halo-lower alkyl, such as trifluoromethyl, carboxy, lower alkoxycarbonyl, carbamoyl, N-lower alkylcarbamoyl, N,N-di(lower alkyl)carbamoyl, cyano, lower alkanoyl, phenyl- or naphthylcarbonyl, lower alkanesulfonyl, sulfamoyl, N-lower alkylsulfamoyl and N,N-di-lower alkylsulfamoyl; $R_5$ preferably being hydrogen; and either $R_7$ and $R_8$ are each hydrogen, or $R_7$ and $R_8$ together form a bond; a tautomer thereof, provided that at least one tautomerisable group is present; or a salt thereof.

Special preference is given to a compound of formula I wherein $R_1$ is hydroxy or, especially, hydrogen;

$R_2$, $R_2'$ and $R_2''$ are each hydrogen;
either
  $R_3$ is hydrogen and
  $R_4$ is hydrogen or lower alkyl, or
  $R_3$ and $R_4$ together are —$(CH_2)_2$— or —$(CH_2)_3$—;
$R_5$ is hydrogen, lower alkyl, such as methyl or ethyl; or naphthyl or phenyl each of which is unsubstituted or substituted by from one to three, especially one or two, radicals selected from lower alkoxy, such as methoxy, halogen, such as bromine or, especially, chlorine or fluorine, lower alkyl, such as methyl or also tert-butyl, and phenyl;
$R_6$ is hydrogen; and
either $R_7$ and $R_8$ are each hydrogen, or $R_7$ and $R_8$ together form a bond; a tautomer thereof, provided that at least one tautomerisable group is present; or a salt thereof.

Greater preference is given to a compound of formula I wherein
  $R_1$ is hydroxy or, especially, hydrogen;
  the radicals $R_2$, $R_2'$ and $R_2''$ are each hydrogen;
either
  $R_3$ is hydrogen and
  $R_4$ is hydrogen or lower alkyl, or
  $R_3$ and $R_4$ together are —$(CH_2)_2$— or —$(CH_2)_3$—;
$R_5$ is hydrogen, lower alkyl, phenyl, 2-, 3- or 4-lower alkoxyphenyl, 2,5-di-lower alkoxyphenyl, 4-fluorophenyl, 4-chlorophenyl, 4-lower alkylphenyl, 4-biphenylyl, or 1- or 2-naphthyl;
$R_6$ is hydrogen; and
either $R_7$ and $R_8$ are each hydrogen, or $R_7$ and $R_8$ together form a bond; or a salt thereof;
lower alkyl in the mentioned radicals being in each case especially methyl or ethyl.

Very great preference is given to a compound of formula I wherein $R_1$, $R_2$, $R_2'$ and $R_2''$ are each hydrogen;
either
  $R_3$ is hydrogen and
  $R_4$ is hydrogen or methyl, or
  $R_3$ and $R_4$ together are —$(CH_2)_2$— or —$(CH_2)_3$—;
$R_5$ is hydrogen, ethyl, phenyl, 2-, 3- or 4-methoxyphenyl, 2,5-dimethoxyphenyl, 4-fluorophenyl, 4-chlorophenyl, 4-methylphenyl, 4-biphenylyl or 2-naphthyl;
$R_6$ is hydrogen; and
either $R_7$ and $R_8$ are each hydrogen, or $R_7$ and $R_8$ together form a bond; or a salt thereof.

Very great preference is given also to a compound of formula I wherein
  $R_1$, $R_2$, $R_2'$ and $R_2''$ are each hydrogen;
  $R_3$ and $R_4$ together are —$(CH_2)_2$— or —$(CH_2)_3$—;
$R_5$ is 3,4-dimethoxyphenyl, 3,4,5-trimethoxyphenyl, 3,5-dimethoxyphenyl, 3,4-dimethylphenyl, 3,5-dimethylphenyl, 2,4-dimethylphenyl, 3,4-dichlorophenyl, 3,5-dichlorophenyl, 2,4-dichlorophenyl or 3,5-di(tert-butyl)phenyl;
$R_6$ is hydrogen; and
$R_7$ and $R_8$ together form a bond; or a salt thereof.

The invention relates especially to the specific compounds described in the Examples, or salts thereof.

The compounds of formula I can be prepared in accordance with methods known per se, for example by a) reacting a compound of formula II

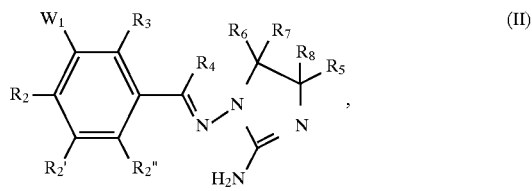

wherein $W_1$ is functionally modified carboxy and the other radicals are as defined for compounds of formula I, or a salt thereof, with hydroxylamine or ammonia of formula III

wherein $R_1$ is hydrogen or hydroxy, or with a salt thereof, functional groups in the starting materials that are not intended to participate in the reaction being, if necessary, in protected form, and removing any protecting groups that are present; or b) reacting a hydroxyimino compound of formula IV

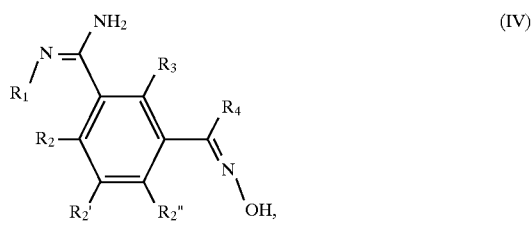

wherein the radicals are as defined for compounds of formula I, or a salt thereof, with an aminoimidazole of formula V

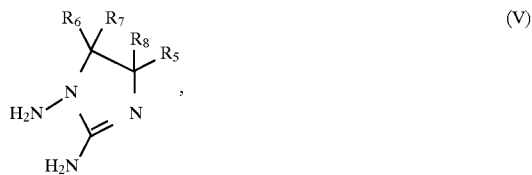

wherein the radicals are as defined for compounds of formula I, or with a salt thereof, functional groups in the starting materials that are not intended to participate in the reaction being, if necessary, in protected form, and removing any protecting groups that are present; or c) for the preparation of a compound of formula I wherein $R_1$ is hydrogen and the other radicals are as defined, reacting an oxo compound of formula VI

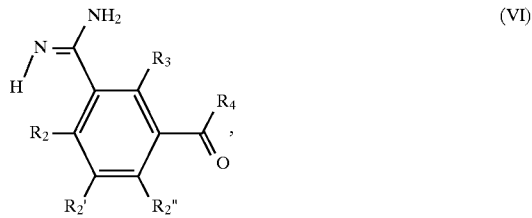

or a reactive derivative thereof, wherein the radicals are as defined for compounds of formula I, or a salt thereof, with an aminoimidazole of formula V

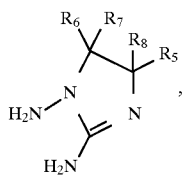
(V)

wherein the radicals are as defined for compounds of formula I, or with a salt thereof, functional groups in the starting materials that are not intended to participate in the reaction being, if necessary, in protected form, and removing any protecting groups that are present;

and, if desired, converting a compound of formula I obtained according to one of processes a), b) or c) into a different compound of formula I, if desired converting a resulting salt of a compound of formula I into the free compound, if desired converting into a salt a free compound of formula I having salt-forming properties that has been obtained directly or according to the last-mentioned step from a different salt, and/or, if desired, separating a resulting mixture of isomers of compounds of formula I into individual isomers.

DETAILED DESCRIPTION OF THE PROCESS

In the following detailed description of the preferred process conditions, the radicals $R_1$, $R_2$, $R_2'$, $R_2''$, $R_3$, $R_4$, $R_5$, $R_6$, $R_7$ and $R_8$ in starting materials, intermediates and end products are each as defined for compounds of formula I, unless indicated otherwise.

Process a): Conversion of a cyano group into a hydroxyamidino or amidino group

In an intermediate of formula II, WI is functionally modified carboxy, preferably imino-alkoxycarbonyl, imino-alkanethiolcarbonyl (both especially in salt form) or, especially, cyano.

In the preparation of amidines of formula I ($R_1$=H or OH), the group $W_1$ in a compound of formula II may be, for example: an acid addition salt of an imino-lower alkyl ester (which corresponds to an imino-lower alkyl ether) or of an imino-lower alkanethiol ester, for example having the radical —C(=NH)—OCH$_5$.HCl or —C(=NH)—SC$_2$H$_5$.HCl. Cyano is, however, preferred.

Reaction of an imino-(lower)alkyl ester or imino-(lower) alkanethiol ester of formula II (in the form of a salt) with ammonia yields a compound of formula I that contains an amidino group ($R_1$=H). Preferably, cyano compounds of formula II are converted, for example, by reaction with an alkali metal amide, such as KNH$_2$, into the corresponding amidino compounds of formula I ($R_1$=H).

N-Hydroxyamidino compounds of formula I ($R_1$=OH) can be prepared in an analogous manner, for example by reacting an imino-(lower)alkyl ester or imino-(lower) alkanethiol ester of formula II (in the form of a salt) with hydroxylamine or a salt thereof.

Preferably, cyano compounds of formula II are converted into the corresponding amidino ($R_1$=H) or, especially, N-hydroxyamidino compounds ($R_1$=OH) of formula I with ammonia or, especially, hydroxylamine of formula III, or salts thereof, for example by reaction in the presence of a base, such as a metal alcoholate, for example the metal alcoholate of a lower alkanol, such as methanol or ethanol, or a metal hydrogen carbonate or, especially, a metal carbonate, preferably a salt of that kind, "metal" denoting an alkali metal, such as sodium or potassium, such as sodium or potassium methanolate or sodium or potassium carbonate. The reaction takes place (i) in the case of metal alcoholates, preferably in the alcohol that matches the metal alcoholate, such as methanol or ethanol, at preferred temperatures of from 0° to 50° C., especially at room temperature; or (ii) in the case of metal carbonates (or also metal hydrogen carbonates), in alcohols, such as methanol or ethanol, N,N-di-lower alkyl-alkanoylamides, such as N,N-dimethylformamide, or water, or mixtures thereof, at preferred temperatures of from 50° C. to the reflux temperature, especially from 75° C. to the reflux temperature.

Starting materials of formula II wherein WI is imino-(lower)alkoxycarbonyl are prepared, for example, by acid-catalyzed reaction of compounds of formula II wherein $W_1$ is cyano with alkanols, especially lower alkanols, for example by reaction with ethanol and hydrochloric acid in, for example, chloroform or diethyl ether. Starting materials of formula II wherein $W_1$ is imino-(lower) alkanethiolcarbonyl are obtained, for example, by first of all converting a compound of formula II wherein WI is cyano into the corresponding thiocarboxamide (in which —C(=S)—NH$_2$ is present instead of $W_1$) by treatment with hydrogen sulfide (for example in pyridine in the presence of a tertiary nitrogen base, such as triethylamine, at temperatures of from 0° to 50° C., for example at approximately 40° C). The thiocarboxamide can then be S-alkylated, for example with the corresponding (lower) alkyl iodide or, preferably, tri (lower) alkyloxonium tetrafluoroborate, preferably under a protective gas, such as argon, in an inert polar solvent, such as a chlorinated hydrocarbon, for example methylene chloride, at preferred temperatures of from 0° to 50° C., especially at approximately room temperature, and thus converted into the imino-(lower) alkanethiol ester hydroiodide (—C(=NH)—S—alkyl—HI) or imino-(lower) alkanethiol ester tetrafluoroborate, respectively.

Compounds of formula II wherein $W_1$ is cyano can be prepared, for example, by reacting a compound of formula VII

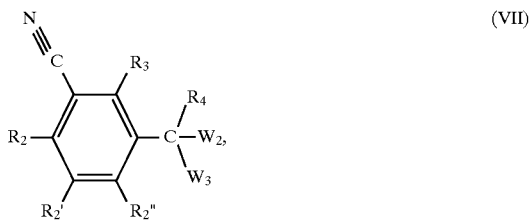
(VII)

wherein $CW_2W_3$ is free or functionally modified or protected carbonyl, with an aminoimidazole of formula V

(V)

wherein the radicals are as defined above (under processes b) and c)).

Functionally modified or protected carbonyl is, for example: di-lower alkoxymethylene ($W_2$ and $W_3$ are each lower alkoxy), $C_1$–$C_2$alkylenedioxymethylene ($W_2$ and $W_3$ together are $C_1$–$C_2$alkylenedioxy), di-lower alkylthiomethylene ($W_2$ and $W_3$ are each lower alkylthio), $C_1$–$C_2$alkylenedithiomethylene ($W_2$ and $W_3$ together are $C_1$–$C_2$alkylenedithio) or, especially, hydroxyiminomethylene. ($W_2$ and $W_3$ together are =N—OH).

In free carbonyl, which (together with hydroxyiminomethylene) is preferred, $W_2$ and $W_3$ together are oxo (=O).

The reaction takes place under the conditions known per se for the reaction of carbonyl derivatives with amino compounds, especially with acid catalysis, preferably analogously to the conditions mentioned under processes b) and c) for the reaction of compounds of formula IV and VI, respectively, with compounds of formula V.

Compounds of formula VII are known or can be prepared in accordance with processes known per se (see, for example, Coll. Czechoslov. Chem. Commun. 43, 3227 (1978)).

For example, compounds of formula VII wherein $CW_2W_3$ is carbonyl and the other radicals are as defined for compounds of formula I can be obtained from compounds of formula VIII

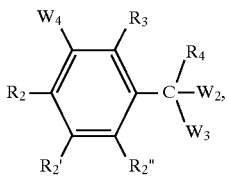

(VIII)

wherein $W_2$ and $W_3$ together are carbonyl and $W_4$ is halogen, especially bromine, or protected amino, for example acetylamino, for example by reaction with copper (I) cyanide (in the case of bromo) or by removal of the acetyl protecting group, diazotisation and reaction with copper(I) cyanide (in the case of acetylamino).

Compounds of formula VII wherein the group $CW_2W_3$ is carbonyl can also be prepared by oxidation, for example with chromium trioxide ($CrO_3$), from the corresponding compounds of formula VIIIa

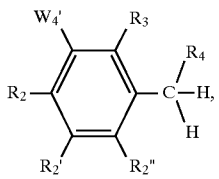

(VIIIa)

wherein $W_4'$ is cyano or halogen, especially bromine, or protected amino, for example acetylamino, and when $W_4'$ is not cyano but one of the other radicals mentioned above, the conversion into a cyano group is carried out analogously to the procedure described above when using compounds of formula VIII.

The corresponding hydroxyimino compounds of formula VII ($W_2$ and $W_3$ together are =N—OH) can then be prepared therefrom by subsequent reaction with hydroxylamine (in free form or in the form of a salt) under customary conditions for the reaction of carbonyl groups with nitrogen bases. In the reaction, an oxo compound of formula VII ($W_2$ and $W_3$=oxo) is reacted with hydroxylamine, which is preferably introduced in an equimolar amount or in an excess, preferably an up to ten-fold excess, relative to the starting material of formula VII, or with a salt thereof, preferably a salt with an inorganic acid, for example a hydrohalic acid, such as hydrofluoric acid, hydrogen chloride, hydrogen bromide or hydrogen iodide, especially hydrogen chloride, with sulfuric acid or a hydrogen sulfate, such as an alkali metal hydrogen sulfate, for example sodium hydrogen sulfate, with phosphoric acid, a hydrogen phosphate or a dihydrogen phosphate, for example an alkali metal hydrogen phosphate or dihydrogen phosphate, such as sodium hydrogen phosphate, disodium hydrogen phosphate, potassium hydrogen phosphate or dipotassium hydrogen phosphate, or a salt with an organic acid, for example with a carboxylic acid, such as a lower alkanecarboxylic acid that is unsubstituted or substituted in the lower alkyl moiety, preferably by halogen, such as fluorine, chlorine or iodine, for example acetic acid, chloroacetic acid, dichloroacetic acid or trifluoro- or trichloro-acetic acid, or with a sulfonic acid, such as a lower alkanesulfonic acid, for example methanesulfonic acid, ethanesulfonic acid or ethanedisulfonic acid, or with an arylsulfonic acid, such as benzene- or naphthalene-sulfonic acid or naphthalene-1,5-disulfonic acid, or a double salt, such as $Zn(NH_2OH)_2Cl_2$ (Crismer's reagent); or is reacted with hydroxylamine prepared in situ, for example from an alcoholic solution of nitric oxide and a tin(II) salt, such as $Sn(II)Cl_2$, in the presence of copper salts, or from the potassium salt of N,O-bis[trimethyl-silyl] hydroxylamine (prepared from $(H_3C)_3Si$—NH—O—Si$(CH_3)_3$ and potassium hydride in tetrahydrofuran, with subsequent freeing of the potassium salt of the compound of formula VII with an acid, for example ammonium chloride); the reaction being carried out in water (in the presence or absence of surfactants), in an aqueous solvent mixture, such as a mixture of water with one or more alcohols, for example methanol or ethanol, di-lower alkyl sulfoxides, such as dimethyl sulfoxide, or di-lower alkyl-lower alkanoylamides, such as dimethylformamide; in organic solvents, such as alcohols, for example methanol or ethanol, di-lower alkyl sulfoxides, such as dimethyl sulfoxide, di-lower alkyl-lower alkanoylamides, such as dimethylformamide, or in sufficiently inert nitriles, such as acetonitrile; a mixture of such organic solvents; or in liquid ammonia, preferably in an aqueous-alcoholic solution, such as methanol/water or ethanol/water; at temperatures of from −78° C. to the reflux temperature of the corresponding reaction mixture, preferably from −30° to 100° C., especially from 5° to 90° C., for example at approximately from 75° to 80° C.; under pressures of approximately from 1 to 10000 bar, preferably, where hydroxylamine salts are used, under normal pressure; in the absence of a base or preferably, where acid salts of hydroxylamine are used, with neutralization of the acid with a base, especially with a hydroxide, such as an alkali metal hydroxide, for example sodium or potassium hydroxide, with a carbonate or hydrogen carbonate, especially an alkali metal or alkaline earth metal carbonate or hydrogen carbonate, for example sodium carbonate, potassium carbonate, sodium hydrogen carbonate, potassium hydrogen carbonate or barium carbonate, with a salt of a weak organic acid, especially an alkali metal or alkaline earth metal salt of a lower alkanecarboxylic acid, for example sodium acetate or potassium acetate, with organic nitrogen bases, especially a secondary or tertiary amine, for example a cyclic 5- or 6-membered secondary or tertiary amine, such as pyrrolidine or pyridine, or with alcoholates, for example alkali metal lower alkyl alcoholates, such as sodium or potassium methanolate, ethanolate or tert-butanolate, or with an anion exchanger, the presence of an alkali metal carbonate being especially preferred; the compound of formula VII wherein $W_2$ and $W_3$ together are hydroxyimino being obtained, preferably directly in crystalline form and, where appropriate, after recrystallization from solvents or solvent mixtures. Preferably, one of the mentioned salts of hydroxylamine, especially the salt of a hydrohalic acid, such as the hydrochloride salt, is reacted in the mentioned organic solvents, especially in an alcohol, such as methanol or ethanol, at the mentioned temperatures, especially at approximately from 75° to 80° C., to yield the corresponding oxime of formula VII, which can be purified or is used further directly.

The other compounds of formula VII, wherein $W_2$ and $W_3$ have one of the meanings mentioned above other than oxo or hydroxyimino, can be prepared from the oxo or hydroxyimino compounds under customary conditions for the preparation of ketals, acetals, thioketals or thioacetals.

Compounds of formula VIII and VIIIa are known or can be prepared in accordance with processes known per se (see, for example, J. Org. Chem. 49, 4226 (1984)).

A further, preferred method for the preparation of a compound of formula II wherein $W_1$ is cyano, $R_7$ and $R_8$ together form a bond and the other radicals are as defined uses as starting material a guanylhydrazone derivative of formula IX

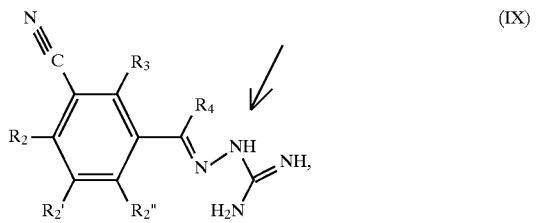

wherein $R_2$, $R_2'$, $R_2''$, $R_3$ and $R_4$ are as defined for compounds of formula I, which is reacted with a compound of formula X

wherein $W_5$ is a nucleofugal leaving group and $R_5$ and $R_6$ are as defined for compounds of formula I, or with a reactive derivative thereof, to form the corresponding compound of formula II.

A nucleofugal leaving group $W_5$ is especially a leaving group selected from hydroxy esterified by a strong inorganic or organic acid, especially hydroxy esterified by a mineral acid, for example a hydrohalic acid, such as hydrochloric, hydrobromic or also hydriodic acid, or also by a strong organic sulfonic acid, such as a lower alkanesulfonic acid that is unsubstituted or substituted by, for example, halogen, such as fluorine, or an aromatic sulfonic acid, for example a benzenesulfonic acid that is unsubstituted or substituted by lower alkyl, such as methyl, halogen, such as bromine, and/or by nitro, such as a methanesulfonic, p-bromotoluenesulfonic or p-toluenesulfonic acid, or hydroxy esterified by hydrazoic acid. The compound in question can also be prepared in situ by replacement of a radical $W_5$, for example chlorine, by another radical $W_5$, for example iodine (preferably using an alkali metal iodide, such as NaI), followed by further reaction in the resulting reaction mixture.

A reactive derivative of a compound of formula X is especially a corresponding acetal or ketal, especially with lower alkanols, such as methanol or ethanol. The carbonyl group in formula X is in that case in the form of a di-lower alkoxymethylene group.

In the case of free compounds of formula X, the reaction preferably takes place in a suitable polar solvent, such as an alcohol, for example methanol or, especially, ethanol, at temperatures of from −10° C. to the reflux temperature, preferably from 0° to 25° C. or at the reflux temperature. If desired or necessary, a tertiary nitrogen base, for example a tri-lower alkylamine, such as triethylamine, is added (especially when the compound of formula IX is not used in a molar excess, for example a two-fold molar excess, relative to the compound of formula X and therefore protons that are released in the reaction can no longer be bound by the excess of the compound of formula IX). Where a reactive derivative of a compound of formula X is used (which is preferred when $R_5$ is hydrogen), the reaction takes place especially in an aprotic solvent, for example an N,N-di-lower alkyl-lower alkanoylamide, such as N,N-dimethylformamide or N,N-dimethylacetamide, in the presence of a strong base, especially an alkali metal hydride, such as potassium hydride or, especially, sodium hydride, at preferred temperatures of from 0° to 100° C., especially from 18° to 60° C., preferably using a protective gas, such as nitrogen or argon, the radical $W_5$ being nucleophilically substituted by the 2'-imino nitrogen of the compound of formula IX (indicated by an arrow in formula IX). The resulting intermediate (containing a reactively derivatized carbonyl group) is then reacted by treatment with an acid, such as a mineral acid, for example a hydrohalic acid, such as HCl, in aqueous solution at preferred temperatures of from 60° C. to the reflux temperature, the corresponding compound of formula II being obtained.

Compounds of formula IX can be prepared in accordance with processes known per se, especially from compounds of formula VII, as defined above, by reaction with aminoguanidine, which is preferably used in approximately equimolar amount or in excess relative to the molar amount of the compound of formula I, especially in an amount that is from 1 to 2 times the molar amount. The reaction takes place under conditions that are customary per se for the reaction of carbonyl groups with nitrogen bases, aminoguanidine preferably being used in the form of the salt of an acid, for example of a hydrohalic acid, such as hydrogen fluoride, hydrogen chloride, hydrogen bromide or hydrogen iodide, especially hydrogen chloride, of sulfuric acid or a hydrogen sulfate, such as an alkali metal hydrogen sulfate, for example sodium hydrogen sulfate, of phosphoric acid, a hydrogen phosphate or a dihydrogen phosphate, for example an alkali metal hydrogen phosphate or dihydrogen phosphate, such as sodium hydrogen phosphate, disodium hydrogen phosphate, potassium hydrogen phosphate or dipotassium hydrogen phosphate, or in the form of a salt with an organic acid, especially with a carboxylic acid, such as a lower alkanecarboxylic acid that is unsubstituted or substituted in the lower alkyl moiety, preferably by halogen, such as fluorine, chlorine or iodine, for example acetic acid, chloroacetic acid, dichloroacetic acid, or trifluoro- or trichloro-acetic acid, with lactic acid or with a sulfonic acid, such as a lower alkanesulfonic acid, for example methanesulfonic acid, ethanesulfonic acid or ethanedisulfonic acid, or an arylsulfonic acid, such as benzene- or naphthalene-sulfonic acid or naphthalene-1,5-disulfonic acid; a salt of a strong acid of the compound of formula III especially being formed in situ, especially from the corresponding salt of a readily volatile weak acid that is capable of being liberated by a strong acid, such as sulfuric acid or, more especially, one of the mentioned hydrohalic acids or methanesulfonic acid, such as a lower alkanecarboxylic acid, for example acetic acid, or especially carbonic acid or hydrogen carbonate, by liberating the weak acid; in water (in the presence or absence of surfactants), in an aqueous solvent mixture, such as a mixture of water with one or more alcohols, for example methanol, ethanol or isopropanol, di-lower alkyl sulfoxides, such as dimethyl sulfoxide, or di-lower alkyl-lower alkanoylamides, such as dimethylformamide, organic solvents, such as one or more alcohols, for example methanol or ethanol, di-lower alkyl sulfoxides, such as dimethyl sulfoxide, di-lower alkyl-lower alkanoylamides, such as dimethylformamide, or sufficiently inert nitrites, such as acetonitrile, or a mixture of such organic solvents, preferably in an aqueous-alcoholic solution, such as in water/methanol, water/ethanol or water/isopropanol; preferably at temperatures of from −20° C. to the reflux temperature of the reaction mixture, especially at temperatures of from room temperature to the reflux temperature of the reaction mixture, more especially at approximately the reflux temperature; the compound of formula VII being obtained directly in free form or, especially, in the form of a salt, preferably of the acid present in the reaction, for example in crystalline form.

Compounds of formula X are known, can be prepared in accordance with processes known per se, or are available commercially.

Corresponding reactive derivatives of compounds of formula X are known, are available commercially or can be prepared in accordance with processes known per se, for example by reaction of a compound of formula X with the corresponding alcohol, if necessary in the presence of dehydrating agents, such as dimethyl sulfide.

Compounds of formula V are known, can be prepared in accordance with processes known per se, or are available commercially. They are prepared, for example, as follows:

Compounds of formula V wherein $R_7$ and $R_8$ together form a bond are prepared from guanidino compounds of formula XI

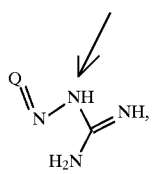

(XI)

wherein Q is an aryl-1-alkylidene radical used as a protecting group, especially benzylidene or also phenyl-1-ethylidene, by reaction with compounds of formula X

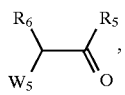

(X)

wherein $W_5$ is a nucleofugal leaving group and $R_5$ and $R_6$ are as defined for compounds of formula I, or with a reactive derivative thereof.

A nucleofugal leaving group $W_5$ is especially a leaving group selected from hydroxy esterified by a strong inorganic or organic acid, especially hydroxy esterified by a mineral acid, for example a hydrohalic acid, such as hydrochloric, hydrobromic or also hydriodic acid, or also by a strong organic sulfonic acid, such as a lower alkanesulfonic acid that is unsubstituted or substituted by, for example, halogen, such as fluorine, or an aromatic sulfonic acid, for example a benzenesulfonic acid that is unsubstituted or substituted by lower alkyl, such as methyl, halogen, such as bromine, and/or by nitro, such as methanesulfonic acid, p-bromotoluenesulfonic acid or p-toluenesulfonic acid, or hydroxy esterified by hydrazoic acid. The compound in question can also be prepared in situ by replacement of a radical $W_5$, for example chlorine, by a different radical $W_5$, for example iodine (preferably using an alkali metal iodide, such as NaI), followed by further reaction in the resulting reaction mixture.

A reactive derivative of a compound of formula X is especially a corresponding acetal or ketal, especially with lower alkanols, such as methanol or ethanol. The carbonyl group in formula X is in that case in the form of, for example, a di-lower alkoxymethylene group.

In the case of free compounds of formula X, the reaction is preferably carried out in a suitable polar solvent, such as an alcohol, for example methanol or, especially, ethanol, at temperatures in the range of from −10° C. to the reflux temperature, preferably from 0° to 20° C. or from 20° C. to the reflux temperature. If desired or necessary, a tertiary nitrogen base, for example a tri-lower alkylamine, such as triethylamine, is added (especially when the compound of formula XI is not used in a molar excess, for example a two-fold molar excess, relative to the compound of formula X and therefore the protons that are released in the reaction cannot be bound by the excess of the compound of formula XI) (see Chem. Ber. 101, 3151–3162 (1968) or J. Het. Chem. 11(3), 327–329 (1974)). In order to obtain a free compound of formula V, the protecting group Q (especially benzylidene) is then removed, preferably either with hydrazine (for example in the form of hydrazine hydrate) in a high-boiling alcohol, such as a di-lower alkylene-di-lower alkanol, such as diethylene glycol, at temperatures of from 100° C. to the reflux temperature, for example from 140° to 170° C., or in the presence of an acid, such as a mineral acid, for example sulfuric acid, phosphoric acid or, especially, a hydrohalic acid, such as HCl or HBr, in aqueous solution at temperatures of from 50° C. to the boiling temperature, especially from 100° to 120° C., preferably with the simultaneous removal by distillation (for example by azeotropic distillation or steam distillation) of the freed compound of the formula Q=O, wherein Q is as defined for compounds of formula XI.

Where a reactive derivative of a compound of formula X is used (which is preferred when $R_5$ is hydrogen), the reaction is preferably carried out in an aprotic solvent, such as an N,N-di-lower alkyl-lower alkanoylamide, for example N,N-dimethylformamide or N,N-dimethylacetamide, in the presence of a strong base, especially an alkali metal hydride, such as potassium hydride or, especially, sodium hydride, at preferred temperatures of from 0° to 100° C., especially from 18° to 60° C., preferably using a protective gas, such as nitrogen or argon, the radical $W_5$ being replaced by the 2'-imino nitrogen of the compound of formula XI (indicated by an arrow in formula XI). The resulting intermediate (containing a reactively derivatized carbonyl group) is then heated by treatment with an acid, such as a mineral acid, for example a hydrogen halide, such as HCl, in aqueous solution at preferred temperatures of from 60° C. to the reflux temperature (for example from 60° C. at the start of the reaction, with heating to 120° C. by the end of the reaction), the compound of formula II being obtained and, where appropriate, the arylalkyl-1-oxo compound Q=O (for example be:nzaldehyde) that is formed simultaneously during the reaction by the removal of protecting groups being removed by azeotropic distillation.

Compounds of formula V wherein $R_5$ is aryl, $R_6$ is hydrogen and $R_7$ and $R_8$ together form a bond can also be prepared from corresponding 2-amino-3-aroylalkyl-5-lower alkyl-1,2,3-oxazolidine bromides with $NH_3$ (at room temperature or with heating) to yield 2-amino-4-aryl-1-lower alkylcarbonyl-imidazoles, hydrolysis of which (for example with water/mineral acid, such as HCl, in the presence.or absence of an alcohol, such as ethanol), with removal of the lower alkanecarboxylic acid, yields a compound of formula V as last defined (see Hetzheim et al., Chem. Ber. 100, 3418–3426 (1967)).

Compounds of formula V wherein $R_5$ and $R_6$ are as defined, and are each especially hydrogen, and wherein $R_7$ and $R_8$ are each hydrogen are prepared especially from imidazolyl ketones or (preferably) imidazolyl thiones of formula XII

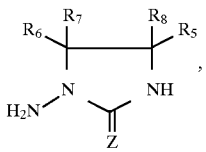

(XII)

wherein Z is oxygen or, preferably, sulfur, $R_5$ and $R_6$ are as defined for compounds of formula I, and are each especially hydrogen, and $R_7$ and $R_8$ are each hydrogen, by reaction with a compound of formula XII $$Y-W_6 \quad (XIII),$$

wherein Y is lower alkyl, especially methyl, and $W_6$ is a nucleofugal leaving group, especially a leaving group selected from hydroxy esterified by a strong inorganic or organic acid, especially hydroxy esterified by a mineral acid, for example a hydrohalic acid, such as hydrochloric, hydrobromic or also hydriodic acid, or preferably by a strong organic sulfonic acid, such as a lower alkanesulfonic acid that is unsubstituted or substituted, for example, by halogen, such as fluorine, or especially an aromatic sulfonic acid, for example a benzenesulfonic acid that is unsubstituted or substituted by lower alkyl, such as methyl, halogen, such as bromine, and/or by nitro, such as methanesulfonic acid, p-bromotoluenesulfonic acid or, especially, p-toluenesulfonic acid, or hydroxy esterified by hydrazoic acid.

The reaction is carried out in suitable solvents or solvent mixtures, such as alcohols, for example a lower alkanol, such as methanol or ethanol, at elevated temperature, for example at the reflux temperature, and yields a compound of formula XIV

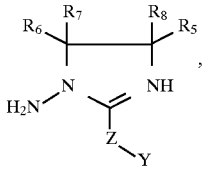

(XIV)

wherein Y is lower alkyl and the other radicals are as defined for compounds of formula XII. The latter is then converted into a compound of formula Va in the form of an acid addition salt

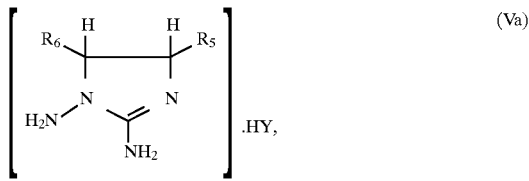

(Va)

wherein Y and $R_5$ and $R_6$ are as defined for compounds of formula XIV, by reaction with ammonia in aqueous solution, if desired in the presence of a polar organic solvent, such as an alcohol, for example methanol, ethanol, isopropanol or a mixture thereof, at preferred temperatures of from 0° C. to the reflux temperature, especially from room temperature to the reflux temperature (see EP 0 327 919). The compound of formula Va corresponds to a compound of formula V wherein $R_5$ and $R_6$ are as defined, and are each especially hydrogen, and $R_7$ and $R_8$ are each hydrogen. The corresponding free compound of formula V can then be obtained from that compound by converting the salt into the free base or into a different salt, analogously to the method described below for compounds of formula I under "Additional process measures", for example by ion exchange on an anion exchanger in the form of the salt of the anion of the acid HY to be introduced (for example anion exchanger based on a styrene/divinylbenzene polymer with quaternary ammonium groups, with the anion $Y^-$ as the counter-ion that is to be introduced).

Other starting materials are known, can be prepared in accordance with processes known per se, or are available commercially.

In all starting materials (for example those of formula II and also III), functional groups that are not intended to participate in the reaction may, independently of one another, be in protected form. If necessary, protecting groups can be removed at suitable stages or not until the stage of the protected precursors of the end products of formula I.

Where specific protecting groups have already been mentioned, those groups are preferred.

The protecting groups for functional groups in starting materials the reaction of which is to be avoided, especially carboxy, amino, hydroxy and mercapto groups, include especially those protecting groups (conventional protecting groups) that are conventionally employed in the synthesis of peptide compounds, and also in the synthesis of cephalosporins and penicillins as well as nucleic acid derivatives and sugars. Those protecting groups may already be present in the precursors and are intended to protect the functional groups in question against undesired secondary reactions, such as acylation, etherification, esterification, oxidation, solvolysis, etc.. In some cases the protecting groups may additionally cause the reactions to proceed selectively, for example stereoselectively. It is characteristic of protecting groups that they can be removed easily, that is to say without undesired secondary reactions taking place, for example by solvolysis, reduction, photolysis, and also enzymatically, for example under physiological conditions, and that they are not present in the end products.

The protection of functional groups by such protecting groups, the protecting groups themselves and the reactions for their removal are described, for example, in standard works, such as J.F.W. McOmie, "Protective Groups in Organic Chemistry", Plenum Press, London and New York 1973, in Th. W. Greene, "Protective Groups in Organic Synthesis", Wiley, New York 1981, in "The Peptides"; Vol. 3 (E. Gross and J. Meienhofer, eds.), Academic Press, London and New York 1981, in "Methoden der organischen Chemie", Houben-Weyl, 4th edition, Vol. 15/I, Georg Thieme Verlag, Stuttgart 1974, in H.-D. Jakubke and H. Jescheit, "Aminosauren, Peptide, Proteine", Verlag Chemie, Weinheim, Deerfield Beach and Basle 1982, and in Jochen Lehmann, "Chemie der Kohlenhydrate: Monosaccharide und Derivate", Georg Thieme Verlag, Stuttgart 1974.

A carboxy group is protected, for example, in the form of an ester group which is selectively removable under mild conditions. A carboxy group protected in esterified form is esterified especially by a lower alkyl group, which is preferably branched in the 1-position of the lower alkyl group or substituted by suitable substituents in the 1- or 2-position of the lower alkyl group.

A protected carboxy group esterified by a lower alkyl group is, for example, methoxycarbonyl or ethoxycarbonyl.

A protected carboxy group esterified by a lower alkyl group that is branched in the 1-position of the lower alkyl group is, for example, tert-lower alkoxycarbonyl, e.g. tert-butoxycarbonyl.

A protected carboxy group esterified by a lower alkyl group that is substituted by suitable substituents in the 1- or 2-position of the lower alkyl group is, for example, 1-aryllower alkoxycarbonyl, such as arylmethoxycarbonyl, having one or two aryl radicals, wherein aryl is phenyl that is unsubstituted or mono-, di- or tri-substituted, for example, by lower alkyl, e.g. tert-lower alkyl, such as tert-butyl, lower alkoxy, e.g. methoxy, hydroxy, halogen, e.g. chlorine, and/or by nitro, for example benzyloxycarbonyl, benzyloxycarbonyl substituted by the mentioned substituents, for example 4-nitrobenzyloxycarbonyl or 4-methoxybenzyloxycarbonyl, diphenylmethoxycarbonyl or diphenylmethoxycarbonyl, substituted by the mentioned substituents, e.g. di(4-methoxyphenyl)methoxycarbonyl, also carboxy esterified by a lower alkyl group, the lower alkyl group being substituted in the 1-or 2-position by suitable substituents, such as 1-lower alkoxy-lower alkoxycarbonyl, for example methoxymethoxycarbonyl, 1-methoxyethoxycarbonyl or 1-ethoxyethoxy-carbonyl, 1-lower alkylthio-lower alkoxycarbonyl, for example 1-methylthiomethoxy-carbonyl or 1-ethylthioethoxycarbonyl, aroylmethoxycarbonyl wherein the aroyl group is benzoyl that is unsubstituted or substituted, for example, by halogen, such as bromine, e.g. phenacyloxycarbonyl, 2-halo-lower alkoxycarbonyl, e.g. 2,2,2-trichloroethoxycarbonyl, 2-bromoethoxycarbonyl or 2-iodoethoxycarbonyl, as well as 2-(trisubstituted silyl)-lower alkoxycarbonyl wherein the substituents are each independently of the others an aliphatic, araliphatic, cycloaliphatic or aromatic hydrocarbon radical that is unsubstituted or substituted, for example, by lower alkyl, lower alkoxy, aryl, halogen and/or by nitro, for example lower alkyl, phenyl-lower alkyl, cycloalkyl or phenyl, each of which is unsubstituted or substituted as above, for example 2-tri-lower alkylsilyl-lower alkoxycarbonyl, such as 2-tri-lower alkylsilylethoxycarbonyl, e.g. 2-trimethylsilylethoxycarbonyl or 2-(di-n-butylmethylsilyl)-ethoxycarbonyl, or 2-triarylsilylethoxycarbonyl, such as triphenylsilylethoxycarbonyl.

A carboxy group can also be protected in the form of an organic silyloxycarbonyl group. An organic silyloxycarbonyl group is, for example, a tri-lower alkylsilyloxycarbonyl group, for example trimethylsilyloxycarbonyl. The silicon atom of the silyloxycarbonyl group can also be substituted by two lower alkyl groups, e.g. methyl groups, and an amino or carboxy group of a second molecule of the compound to be protected. Compounds having such protecting groups can be prepared, for example, using corresponding tri-lower alkylhalosilanes, such as tert-butyl-dimethylchlorosilane, as silylating agent.

A carboxy group is also protected in the form of an internal ester with a hydroxy group present at a suitable distance, for example in the γ-position, with respect to the carboxy group, that is to say in the form of a lactone, preferably a γ-lactone.

A protected carboxy group is preferably tert-lower alkoxycarbonyl, for example tertbutoxycarbonyl, benzyloxycarbonyl, 4-nitrobenzyloxycarbonyl, 9-fluorenylmethoxy-carbonyl or diphenylmethoxycarbonyl, or a carboxy group protected in the form of a lactone, especially a γ-lactone.

A protected amino group is protected by an amino-protecting group, for example in the form of an acylamino, arylmethylamino, etherified mercaptoamino, 2-acyl-lower alk-1-enylamino or silylamino group, or in the form of an azido group.

In an acylamino group acyl is, for example, the acyl radical of an organic carboxylic acid having, for example, up to 18 carbon atoms, especially of a lower alkanecarboxylic acid that is unsubstituted or substituted by, for example, halogen or aryl, or of a benzoic acid that is unsubstituted or substituted by, for example, halogen, lower alkoxy or nitro, or preferably of a carbonic acid semiester. Such acyl groups are preferably lower alkanoyl, such as formyl, acetyl, propionyl or pivaloyl, halo-lower alkanoyl, for example 2-halo-acetyl, such as 2-chloro-, 2-bromo-, 2-iodo-, 2,2,2-trifluoro- or 2,2,2-trichloro-acetyl, benzoyl that is unsubstituted or substituted by, for example, halogen, lower alkoxy or nitro, such as benzoyl, 4-chlorobenzoyl, 4-methoxybenzoyl or 4-nitrobenzoyl, lower alkoxycarbonyl, lower alkoxycarbonyl that is preferably branched at the 1-position of the lower alkyl radical or suitably substituted at the 1- or 2-position, for example tert-lower alkoxycarbonyl, such as tert-butoxycarbonyl, 1-aryl-lower alkoxycarbonyl, such as arylmethoxycarbonyl, having one, two or three aryl radicals which are phenyl that is unsubstituted or mono- or poly-substituted, for example, by lower alkyl, especially tert-lower alkyl, such as tert-butyl, lower alkoxy, such as methoxy, hydroxy, halogen, such as chlorine, and/or by nitro, for example benzyloxycarbonyl, 4-nitrobenzyloxycarbonyl, di-phenylmethoxycarbonyl, 9-fluorenylmethoxycarbonyl or di(4-methoxyphenyl) methoxy-carbonyl, aroylmethoxycarbonyl wherein the aroyl group is preferably benzoyl that is unsubstituted or substituted by, for example, halogen, such as bromine, for example phenacyloxycarbonyl, 2-halo-lower alkoxycarbonyl, for example 2,2,2-trichloroethoxy-carbonyl, 2-bromoethoxycarbonyl or 2-iodoethoxycarbonyl, 2-(trisubstituted silyl)-lower alkoxycarbonyl, for example 2-tri-lower alkylsilyl-lower alkoxycarbonyl, such as 2-tri-methylsilylethoxycarbonyl or 2-(di-n-butylmethylsilyl) ethoxycarbonyl, or triarylsilyl-lower alkoxycarbonyl, for example 2-triphenylsilylethoxycarbonyl.

In an arylmethylamino group, for example a mono-, di- or, especially, tri-arylmethylamino group, the aryl radicals are especially unsubstituted or substituted phenyl radicals. Such groups are, for example, benzyl-, diphenylmethyl- or, especially, trityl-amino.

In an etherified mercaptoamino group, the mercapto group is especially in the form of substituted arylthio or aryl-lower alkylthio wherein aryl is, for example, phenyl that is unsubstituted or substituted, for example, by lower alkyl, such as methyl or tert-butyl, lower alkoxy, such as methoxy, halogen, such as chlorine, and/or by nitro, for example 4-nitrophenylthio.

In a 2-acyl-lower alk-1-enyl radical that may be used as an amino-protecting group, acyl is, for example, the corresponding radical of a lower alkanecarboxylic acid, of a benzoic acid that is unsubstituted or substituted, for example, by lower alkyl, such as methyl or tert-butyl, lower alkoxy, such as methoxy, halogen, such as chlorine, and/or by nitro, or especially of a carbonic acid semiester, such as a carbonic acid lower alkyl semiester. Corresponding protecting groups are especially 1-lower alkanoyl-lower alk-1-en-2-yl, for example 1-lower alkanoyl-prop-1-en-2-yl, such as 1-acetyl-prop-1-en-2-yl, or lower alkoxycarbonyl-lower alk-1-en-2-yl, for example lower alkoxycarbonyl-prop-1-en-2-yl, such as 1-ethoxycarbonyl-prop-1-en-2-yl.

A silylamino group is, for example, a tri-lower alkylsilylamino group, for example tri-methylsilylamino or tert-butyl-dimethylsilylamino. It is also possible for the silicon atom of the silylamino group to be substituted by only two lower alkyl groups, for example methyl groups, and by the amino group or carboxy group of a second molecule of formula I. Compounds having such protecting groups may be prepared, for example, using the corresponding chlorosilanes, such as tert-butyl-dimethylchlorosilane, as silylating agent.

An amino group can also be protected by conversion into the protonated form; suitable anions are especially anions of strong inorganic acids, such as sulfuric acid, phosphoric acid or hydrohalic acids, for example the chlorine or bromine anion, or of organic sulfonic acids, such as p-toluenesulfonic acid.

Preferred amino-protecting groups are lower alkoxycarbonyl, phenyl-lower alkoxycarbonyl, fluorenyl-lower alkoxycarbonyl, 2-lower alkanoyl-lower alk-l-en-2-yl or lower alkoxycarbonyl-lower alk-1-en-2-yl, especially tert-butoxycarbonyl or benzyloxycarbonyl.

A hydroxy group can be protected, for example, by an acyl group, for example lower alkanoyl that is unsubstituted or substituted by halogen, such as chlorine, such as acetyl or 2,2-dichloroacetyl, or especially by an acyl radical of a carbonic acid semiester mentioned for protected amino groups. A hydroxy group can be protected also by tri-lower alkylsilyl, for example trimethylsilyl, triisopropylsilyl or tert-butyl-dimethylsilyl, a readily removable etherifying group, for example an alkyl group, such as tert-lower alkyl, for example tert-butyl, an oxa- or a thia-aliphatic or -cycloaliphatic, especially 2-oxa- or 2-thia-aliphatic or -cycloaliphatic, hydrocarbon radical, for example 1-lower alkoxy-lower alkyl or 1-lower alkylthio-lower alkyl, such as methoxymethyl, 1-methoxyethyl, 1-ethoxyethyl, methylthiomethyl, 1-methylthioethyl or 1-ethylthioethyl, or 2-oxa- or 2-thiacycloalkyl having from 5 to 7 ring atoms, such as 2-tetrahydrofuryl or 2-tetrahydropyranyl, or a corresponding thia analogue, as well as by 1-phenyl-lower alkyl, such as benzyl, diphenylmethyl or trityl, it being possible for the phenyl radicals to be substituted, for example, by halogen, e.g. chlorine, lower alkoxy, e.g. methoxy, and/or by nitro. A preferred hydroxy-protecting group is, for example, 2,2,2-trichloroethoxycarbonyl, 4-nitrobenzyloxy-carbonyl, diphenylmethoxycarbonyl, benzyl or trityl.

Two hydroxy groups occurring in a molecule, especially adjacent hydroxy groups, or adjacent hydroxy and amino groups can be protected, for example, by divalent protecting groups, such as a methylene group that is preferably substituted, for example by one or two lower alkyl radicals or by oxo, for example by unsubstituted or substituted alkylidene, e.g. lower alkylidene, such as isopropylidene, cycloalkylidene, such as cyclohexylidene, a carbonyl group or benzylidene.

A hydroxy group that is adjacent to a carboxy group can be protected by the formation of an internal ester (lactone), especially a γ-lactone.

A protected hydroxy group is preferably protected by tri-lower alkylsilyl or in the form of a lactone, especially by tert-butyl-dimethylsilyl or in the form of a γ-lactone.

A mercapto group, for example in cysteine, can be protected especially by S-alkylation with unsubstituted or substituted alkyl radicals, silylation, thioacetal formation, S-acylation or by the formation of asymmetrical disulfide groupings. Preferred mercapto-protecting groups are, for example, benzyl that is unsubstituted or substituted in the phenyl moiety, for example by methoxy or by nitro, such as 4-methoxybenzyl, diphenylmethyl that is unsubstituted or substituted in the phenyl moiety, for example by methoxy, such as di(4-methoxyphenyl)methyl, triphenylmethyl, pyridyldiphenylmethyl, trimethylsilyl, benzylthiomethyl, tetrahydropyranyl, acylaminomethyl, such as acetamidomethyl, iso-butyrylacetamidomethyl or 2-chloroacetamidomethyl, benzoyl, benzyloxycarbonyl or alkylaminocarbonyl, especially lower alkylaminocarbonyl, such as ethylaminocarbonyl, as well as lower alkylthio, such as S-ethylthio or S-tert-butylthio, or S-sulfo.

The person skilled in the art is familiar with protecting groups that are suitable for the reaction conditions in question and can therefore select them without difficulty.

For the removal of protecting groups, the reaction conditions already mentioned specifically are preferably employed.

The removal of protecting groups that are not constituents of the desired intermediate or, especially, of the end product of formula I is effected in a manner known per se, for example by means of solvolysis, especially hydrolysis, alcoholysis or acidolysis, or by means of reduction, especially hydrogenolysis or by means of other reducing agents, as well as photolysis, as appropriate stepwise or simultaneously, it being possible also to use enzymatic methods. The removal of the protecting groups is described, for example, in the standard works mentioned hereinabove in the section relating to protecting groups.

For example, protected carboxy, for example lower alkoxycarbonyl (preferably branched in the 1-position), such as tert-lower alkoxycarbonyl, lower alkoxycarbonyl substituted at the 2-position by a trisubstituted silyl group or at the 1-position by lower alkoxy or by lower alkylthio, or unsubstituted or substituted diphenylmethoxycarbonyl can be converted into free carboxy by treatment with a suitable acid, such as formic acid, acetic acid, hydrochloric acid or trifluoroacetic acid, where appropriate with the addition of a nucleophilic compound, such as phenol or anisole. Unsubstituted or substituted benzyloxycarbonyl can be freed, for example, by means of hydrogenolysis, that is to say by treatment with hydrogen in the presence of a metallic hydrogenation catalyst, such as a palladium catalyst. Moreover, suitably substituted benzyloxycarbonyl, such as 4-nitrobenzyloxycarbonyl, can be converted into free carboxy also by reduction, for example by treatment with an alkali metal dithionite, such as sodium dithionite, or with a reducing metal, for example zinc, or with a reducing metal salt, such as a chromium(II) salt, for example chromium(II) chloride, customarily in the presence of a hydrogen-yielding agent that, together with the metal, is capable of producing nascent hydrogen, such as an acid, especially a suitable carboxylic acid, such as an unsubstituted or substituted, for example hydroxy-substituted, lower alkanecarboxylic acid, for example acetic acid, formic acid, glycolic acid, diphenylglycolic acid, lactic acid, mandelic acid, 4-chloromandelic acid or tartaric acid, or in the presence of an alcohol or thiol, water preferably being added. By treatment with a reducing metal or metal salt, as described above, 2-halo-lower alkoxycarbonyl (where appropriate after conversion of a 2-bromo-lower alkoxycarbonyl group into a corresponding 2-iodo-lower alkoxycarbonyl group) or aroylmethoxycarbonyl can also be converted into free carboxy. Aroylmethoxycarbonyl can be cleaved also by treatment with a nucleophilic, preferably salt-forming, reagent, such as sodium thiophenolate or sodium iodide. The carboxy group can be freed from 1-aryl-lower alkoxycarbonyl, for example arylmethoxycarbonyl, such as benzyloxycarbonyl, also by hydrolysis in the presence of a base, such as an alkali metal hydroxide, for example sodium or potassium hydroxide. 2-(Trisubstituted silyl)-lower alkoxycarbonyl, such as 2-tri-lower alkylsilyl-lower alkoxycarbonyl, can also be converted into free carboxy by treatment with a salt of hydrofluoric acid that yields the fluoride anion, such as an alkali metal fluoride, for example sodium or potassium fluoride, where appropriate in the presence of a macrocyclic polyether ("crown ether"), or with a fluoride of an organic quaternary base, such as a tetra-lower alkylammonium fluoride or tri-lower alkylaryl-lower alkylammonium fluoride, for example tetraethylammonium fluoride or tetrabutylammonium fluoride, in the presence of an aprotic, polar solvent, such as dimethyl sulfoxide, N,N-dirnethylformamide or N,N-dimethylacetamide. Carboxy protected in the form of organic silyloxycarbonyl, such as tri-lower alkylsilyloxycarbonyl, for example trimethylsilyloxycarbonyl, can be freed in customary manner by solvolysis, for example by treatment with water, an alcohol or an acid, or, furthermore, a fluoride, as described above. Esterified carboxy can also be freed enzymatically, for example by means of esterases or suitable peptidases, for example esterified arginine or lysine, such as lysine methyl ester, by using trypsin. Carboxy protected in the form of an internal ester, such as in the form of the γ-lactone, can be freed by hydrolysis in the presence of a hydroxide-containing base, such as an alkaline earth metal hydroxide or, especially, an alkali metal hydroxide, for example NaOH, KOH or LiOH, more especially LiOH, the correspondingly protected hydroxy group being freed at the same time.

A protected amino group is freed in a manner known per se and, according to the nature of the protecting groups, in various ways, preferably by means of solvolysis or reduction. Lower alkoxycarbonylamino, such as tert-butoxycarbonylamino can be cleaved in the presence of acids, for example mineral acids, e.g. a hydrogen halide, such as hydrogen chloride or hydrogen bromide, especially hydrogen bromide, or sulfuric or phosphoric acid, preferably hydrogen chloride, or in the presence of relatively strong organic acids, such as formic acid, trichloroacetic acid or trifluoroacetic acid, in polar solvents, for example water or a carboxylic acid, such as acetic acid or formic acid, halogenated hydrocarbons, such as chlorinated lower alkanes, for example dichloromethane or chloroform, or ethers, preferably cyclic ethers, such as dioxane, or in organic carboxylic acids that are liquid at the reaction temperature, without solvents, for example in formic acid. 2-Halo-lower alkoxycarbonylamino (where appropriate after conversion of a 2-bromo-lower alkoxycarbonylamino group into a 2-iodo-lower alkoxycarbonylamino group), aroyl-methoxycarbonylamino or 4-nitrobenzyloxycarbonylamino can be cleaved, for example, by treatment with a suitable reducing agent, such as zinc in the presence of a suitable carboxylic acid, such as aqueous acetic acid. Aroylmethoxycarbonylamino can be cleaved also by treatment with a nucleophilic, preferably salt-forming, reagent, such as sodium thiophenolate, and 4-nitrobenzyloxycarbonylamino can be cleaved also by treatment with an alkali metal dithionite, for example sodium dithionite. Unsubstituted or substituted diphenylmethoxycarbonylamino, tert-lower alkoxycarbonylamino or 2-(trisubstituted silyl)-lower alkoxycarbonylamino, such as 2-tri-lower alkylsilyl-lower alkoxycarbonylamino, can be cleaved by treatment with a suitable acid, for example formic acid or tri-fluoroacetic acid, for example in a halogenated hydrocarbon, such as methylene chloride or chloroform (especially when hydroxy protected by benzyl is not to be freed at the same time), 1-aryl-lower alkoxycarbonylamino, such as unsubstituted or substituted benzyloxycarbonylamino, can be cleaved, for example, by means of hydrogenolysis, that is to say by treatment with hydrogen in the presence of a suitable hydrogenation catalyst, such as a palladium catalyst, for example bonded to a carrier, such as carbon, preferably in polar solvents, such as di-lower alkyl-lower alkanoylamides, for example dimethylformamide, ethers, such as cyclic ethers, for example dioxane, esters, such as lower alkanoic acid lower alkyl esters, for example ethyl acetate, or alcohols, such as methanol, ethanol or propanol, methanol being especially preferred, preferably approximately at room temperature, unsubstituted or substituted triarylmethylamino or formylamino can be cleaved, for example, by treatment with an acid, such as a mineral acid, for example hydrochloric acid, or an organic acid, for example formic acid, acetic acid or trifluoroacetic acid, where appropriate in the presence of water, and triphenylaminomethyl can be cleaved especially by hydrogenolysis with a noble metal or noble metal oxide as catalyst, such as platinum, palladium or, especially, palladium hydroxide, the catalyst preferably being bonded to a carrier, such as carbon, silica gel or aluminum oxide, in inert solvents, such as an ether, preferably a lower alkyl-lower alkanoate, such as ethyl acetate, at temperatures of from 20° to 80° C., especially from 50° to 70° C., if necessary under elevated pressure, for example approximately from 1 to 10 bar, and an amino group protected in the form of silylamino can be freed, for example, by means of hydrolysis or alcoholysis. An amino group protected by 2-haloacetyl, for example 2-chloroacetyl, can be freed by treatment with thiourea in the presence of a base, or with a thiolate salt, such as an alkali metal thiolate of thiourea, and subsequent solvolysis, such as alcoholysis or hydrolysis, of the resulting substitution product. An amino group protected by 2-(trisubstituted silyl)-lower alkoxycarbonyl, such as 2-tri-lower alkylsilyl-lower alkoxycarbonyl, can be converted into the free amino group also by treatment with a salt of hydrofluoric acid that yields fluoride anions, as indicated above in connection with the freeing of a correspondingly protected carboxy group. Likewise, silyl, such as trimethylsilyl or tert-butyldimethylsilyl, bonded directly to a hetero atom, such as nitrogen, can be removed using fluoride ions, preferably with a fluoride of an organic quaternary nitrogen base, such as a tetra-lower alkylammonium fluoride or tri-lower alkylaryl-lower alkylammonium fluoride, for example tetraethylammonium fluoride or tetrabutylammonium fluoride, in the presence of an aprotic, polar solvent, such as dimethyl sulfoxide or N,N-dimethylacetamide, or especially an ether, such as tetrahydrofuran, at temperatures of from 0° to 50° C., especially at about room temperature.

Amino protected in the form of an azido group is converted into free amino, for example, by reduction, for example by catalytic hydrogenation with hydrogen in the presence of a hydrogenation catalyst, such as platinum oxide, palladium or Raney nickel, by reduction using mercapto compounds, such as dithiothreitol or mercaptoethanol, or by treatment with zinc in the presence of an acid, such as acetic acid. The catalytic hydrogenation is preferably carried out in an inert solvent, such as a halogenated hydrocarbon, for example methylene chloride, or in water or a mixture of water and an organic solvent, such as an alcohol or dioxane, at approximately from 20° C. to 25° C., or with cooling or heating.

A hydroxy or mercapto group protected by a suitable acyl group, by a tri-lower alkylsilyl group or by unsubstituted or substituted 1-aryl-(such as 1-phenyl)-lower alkyl is freed analogously to a correspondingly protected amino group. A hydroxy or mercapto group protected by 2,2-dichloroacetyl is freed, for example, by basic hydrolysis, and a hydroxy or mercapto group protected by tert-lower alkyl or by a 2-oxa- or 2-thia-aliphatic or -cycloaliphatic hydrocarbon radical is freed by acidolysis, for example by treatment with a mineral acid or a strong carboxylic acid, for example trifluoroacetic acid. A hydroxy group protected by benzyloxy is freed, for example, by hydrogenolysis, that is to say by treatment with hydrogen in the presence of a suitable hydrogenation catalyst, such as a palladium catalyst, for example bonded to a carrier, such as carbon, preferably in polar solvents, such as di-lower alkyl-lower alkanoylamides, for example dimethylformamide, ethers, such as cyclic ethers, for example dioxane, esters, such as lower alkylalkanoates, for example ethyl acetate, or alcohols, such as methanol, ethanol or propanol, with methanol being especially preferred, preferably at about room temperature. Mercapto protected by pyridyldiphenylmethyl can be freed, for example, using mercury(II) salts at pH 2-6 or by zinc/acetic acid or electrolytic reduction; acetamidomethyl and isobutyrylamidomethyl can be removed, for example, by reaction with mercury(II) salts at pH 2–6; 2-chloroacetamidomethyl can be removed, for example, using 1-piperidinothiocarboxamide; and S-ethylthio, S-tert-butylthio and S-sulfo can be removed, for example, by thiolysis with thiophenol, thioglycolic acid, sodium thiophenolate or 1,4-dithiothreitol. Two hydroxy groups or adjacent amino and hydroxy groups which are protected together by means of a divalent protecting group, preferably, for example, by a methylene group mono- or di-substituted by lower alkyl, such as lower alkylidene, for example isopropylidene, cycloalkylidene, for example cyclohexylidene, or benzylidene, can be freed by acid solvolysis, especially in the presence of a mineral acid or a strong organic acid. A tri-lower alkylsilyl group is likewise removed by acidolysis, for example by a mineral acid, preferably hydrofluoric acid, or a strong carboxylic acid. Hydroxy can be freed from tri-lower alkylsilyloxy preferably also by treatment with a salt of hydrofluoric acid that yields the fluoride anion, such as an alkali metal fluoride, for example sodium or potassium fluoride, where appropriate in the presence of a macrocyclic polyether ("crown ether"), or with a fluoride of an organic quaternary base, such as a tetra-lower alkylammonium fluoride or tri-lower alkylaryl-lower alkylammonium fluoride, for example tetraethylammonium fluoride or tetrabutylammonium fluoride, in the presence of an aprotic polar solvent, such as dimethyl sulfoxide or N,N-dimethylacetamide. 2-Halo-lower alkoxycarbonyl is removed using the above-mentioned reducing agents, for example a reducing metal, such as zinc, reducing metal salts, such as chromium(II) salts, or using sulfur compounds, for example sodium dithionite or, preferably, sodium sulfide and carbon disulfide. Esterified hydroxy groups, for example lower alkanoyloxy, such as acetyloxy, can also be freed using esterases, and acylated amino can be freed, for example, using suitable peptidases.

The temperatures at which the protected functional groups are freed are preferably from −80° C. to the boiling temperature of the reaction mixture, especially from −80° to 110° C., more especially from −20° to 50° C., for example from 10° to 35° C., such as approximately room temperature, or at from 80° C. to the boiling temperature of the reaction mixture in question, for example at approximately 100° C.

When several protected functional groups are present, the protecting groups may, if desired, be so selected that it is possible to remove more than one such group simultaneously, for example by means of acidolysis, such as by treatment with trifluoroacetic acid, or by means of hydrogen and a hydrogenation catalyst, such as a palladium-on-carbon catalyst. Conversely, the groups may also be so selected that they are not all removed simultaneously but can be removed in a desired sequence, in which case the corresponding intermediates are obtained.

Process b) - Formation of a Schiff's base by reaction of a hydroxyimino compound with an amino compound In compounds of formulae IV and V, functional groups that are not intended to participate in the reaction may, if necessary, be in protected form; protecting groups, processes for their introduction and processes for their removal from resulting protected compounds of formula I are analogous to those mentioned in the detailed description of process a).

In the starting materials of formula IV, and hence in the products of formula I, the radical $R_1$ is preferably hydroxy.

The reaction between compounds of formula IV (hydroxyimino compound) and formula V (aminoimidazole) takes place under conditions that are known per se, the aminoimidazole of formula V preferably being used in an approximately equimolar amount or in excess relative to the molar amount of the compound of formula IV, especially in an amount that is from 0.95 times to twice the molar amount—in particular, the reaction takes place under conditions that are customary for the reaction of carbonyl compounds with nitrogen bases; preferably in the presence of acids, for example of a hydrohalic acid, such as hydrogen fluoride, hydrogen chloride, hydrogen bromide or hydrogen iodide, especially hydrogen chloride, of sulfuric acid or a hydrogen sulfate, such as an alkali metal hydrogen sulfate, for example sodium hydrogen sulfate, of phosphoric acid, a hydrogen phosphate or a dihydrogen phosphate, for example an alkali metal hydrogen phosphate or dihydrogen phosphate, such as sodium hydrogen phosphate, disodium hydrogen phosphate, potassium hydrogen phosphate or dipotassium hydrogen phosphate, or of an organic acid, especially a carboxylic acid, such as a lower alkanecarboxylic acid that is unsubstituted or substituted in the lower alkyl moiety, preferably by halogen, such as fluorine, chlorine or iodine, for example acetic acid, chloroacetic acid, dichloroacetic acid or trifluoro- or trichloroacetic acid, of lactic acid or of a sulfonic acid, such as a lower alkanesulfonic acid, for example methanesulfonic acid, ethanesulfonic acid or ethanedisulfonic acid, or an arylsulfonic acid, such as benzene- or naphthalene-sulfonic acid or naphthalene-1,5-disulfonic acid; there being used especially a strong acid, such as sulfuric acid or, more especially, one of the mentioned hydrohalic acids or methanesulfonic acid; in water (in the presence or absence of surfactants) or in an aqueous solvent mixture, such as a mixture of water with one or more alcohols, for example methanol, ethanol or, especially, isopropanol, or also di-lower alkyl sulfoxides, such as dimethyl sulfoxide, or di-lower alkyl-lower alkanoylamides, such as dimethylformamide, organic solvents, such as one or more alcohols, for example methanol or ethanol, di-lower alkyl sulfoxides, such as dimethyl sulfoxide, di-lower alkyl-lower alkanoylamides, such as dimethylformamide, or in sufficiently inert nitriles, such as acetonitrile, a mixture of such organic solvents, preferably in an aqueous-alcoholic solution, such as in water/methanol, water/ethanol or, especially, water/isopropanol; preferably at temperatures of from −20° C. to the reflux temperature of the reaction mixture, especially at temperatures of from room temperature to the reflux temperature of the reaction mixture, more especially at approximately from 80° C. to the reflux temperature; the compound of formula I (where appropriate after customary working up) being obtained directly in free form or, especially, in the form of a salt, preferably of the acid present in the reaction, for example in crystalline form. Special preference is given to the reaction of the hydroxyimino compound of formula IV and the aminoimidazole of formula V with aqueous HCl in isopropanol at temperatures of from 80° C. to the reflux temperature (for example not higher than 120° C.).

The preparation of the starting materials of formula V has already been described in connection with the preparation of starting materials for process a).

Hydroxyimino compounds of formula IV are preferably prepared from compounds of formula VII, which are described as starting materials in process a), wherein $W_2$ and $W_3$ are especially together oxo and the other radicals are as defined therein, different procedures being possible.

For example, compounds of formula IV wherein $R_1$ is hydrogen and the other radicals are as defined can first be converted into compounds of formula VI

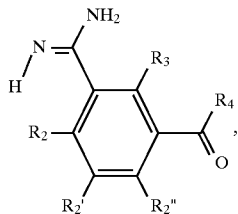

wherein the radicals are as defined for compounds of formula I, by the reaction of cyano compounds of formula VII wherein $W_2$ and $W_3$ are especially together oxo, while $R_2$, $R_2'$, $R_2''$, $R_3$ and $R_4$ are as defined for compounds of formula I, with ammonia or with a salt thereof. The reaction is preferably carried out starting from the starting materials of formula VII by acid-catalysed reaction of the cyano group either a) with alkanols, especially lower alkanols, for example by reaction with ethanol and hydrochloric acid in, for example, chloroform or diethyl ether, via the corresponding compound wherein there is an irnino-(lower) alkoxycarbonyl radical (preferably in salt form) instead of the cyano group; or b) preferably by treatment with hydrogen sulfide (for example in pyridine in the presence of a tertiary nitrogen base, such as triethylamine, at temperatures of from 0° to 50° C., for example at approximately 40° C.) via the corresponding thiocarboxamide (the group —C(=S)—NH$_2$ is present in formula VII instead of the cyano group), which is then converted into the corresponding compound with an imino-(lower) alkanethiolcarbonyl group, preferably the corresponding imino-(lower) alkanethiol ester salt, for example by S-alkylating the thiocarboxamide with the corresponding (lower) alkyl iodide or, preferably, tri-(lower) alkyloxonium tetrafluoroborate, preferably under a protective gas, such as argon, in an inert polar solvent, such as a chlorinated hydrocarbon, for example methylene chloride, at preferred temperatures of from 0° to 50° C., especially at approximately room temperature, and thus converting it into the imino-(lower) alkanethiol ester hydroiodide (—C(=NH)—S-alkyl.HI) or imino-(lower) alkanethiol ester tetrafluoroborate, respectively;

and then, by reaction of the imino-(lower) alkyl ester derivative or the imino-(lower) alkanethiol ester derivative of the compound of formula VII (in salt form) with ammonia or salts thereof, the corresponding compound of formula VI containing the amidino group ($R_1$=H) is obtained. The reaction with ammonia—with or without previous isolation of the imino-(lower) alkyl ester derivative or imino-(lower) alkanethiol ester derivative of the compound of formula VII (in salt form)—is preferably carried out in a suitable organic solvent, such as an alcohol, for example ethanol, at temperatures of from 40° C. to the reflux temperature, preferably at the reflux temperature, in the presence of acids, for example a mineral acid, such as sulfuric acid, phosphoric acid or, especially, a hydrohalic acid, such as HCl; in an especially preferred form of the process, ammonia is added directly in the form of the corresponding salt.

The resulting compound of formula VI is then converted, by conversion of the carbonyl group into the hydroxy imino group, into the corresponding compound of formula IV wherein $R_1$ is hydrogen and the other radicals are as defined. In the reaction, an oxo compound of formula VI is reacted with hydroxylamine, which is preferably introduced in an equimolar amount or in an excess, preferably an up to ten-fold excess, relative to the starting compound of formula VII, or with a salt thereof, preferably a salt with an inorganic acid, for example a hydrohalic acid, such as hydrofluoric acid, hydrogen chloride, hydrogen bromide or hydrogen iodide, especially hydrogen chloride, with sulfuric acid or a hydrogen sulfate, such as an alkali metal hydrogen sulfate, for example sodium hydrogen sulfate, with phosphoric acid, a hydrogen phosphate or a dihydrogen phosphate, for example an alkali metal hydrogen phosphate or dihydrogen phosphate, such as sodium hydrogen phosphate, disodium hydrogen phosphate, potassium hydrogen phosphate or dipotassium hydrogen phosphate, or a salt with an organic acid, for example with a carboxylic acid, such as a lower alkanecarboxylic acid that is unsubstituted or substituted in the lower alkyl moiety, preferably by halogen, such as fluorine, chlorine or iodine, for example acetic acid, chloroacetic acid, dichloroacetic acid or trifluoro- or tri-chloroacetic acid, or with a sulfonic acid, such as a lower alkanesulfonic acid, for example methanesulfonic acid, ethanesulfonic acid or ethanedisulfonic acid, or with an arylsulfonic acid, such as benzene- or naphthalene-sulfonic acid or naphthalene-1,5-di-sulfonic acid, or a double salt, such as $Zn(NH_2OH)_2Cl_2$ (Crismer's reagent); or is reacted with hydroxylamine prepared in situ, for example from an alcoholic solution of nitric oxide and a tin(II) salt, such as $Sn(II)Cl_2$, in the presence of copper salts, or from the potassium salt of N,O-bis[trimethylsilyl]hydroxylamine (prepared from $(H_3C)_3Si$—NH—O—$Si(CH_3)_3$ and potassium hydride in tetrahydrofuran, with subsequent freeing of the potassium salt of the compound of formula VI with an acid, for example ammonium chloride); the reaction being carried out in water (in the presence or absence of surfactants), in an aqueous solvent mixture, such as a mixture of water with one or more alcohols, for example methanol or ethanol, di-lower alkyl sulfoxides, such as dimethyl sulfoxide, or di-lower alkyl-lower alkanoylamides, such as dimethylformamide; in organic solvents, such as alcohols, for example methanol or ethanol, di-lower alkyl sulfoxides, such as dimethyl sulfoxide, di-lower alkyl-lower alkanoylamides, such as dimethylformamide, or in sufficiently inert nitriles, such as acetonitrile; a mixture of such organic solvents; or in liquid ammonia, preferably in an aqueous-alcoholic solution, such as methanol/water or ethanol/water; at temperatures of from −78° C. to the reflux temperature of the corresponding reaction mixture, preferably from −30° to 100° C., especially from 5° to 90° C., for example at approximately from 75° to 80° C.; under pressures of approximately from 1 to 10000 bar, preferably, where hydroxylamine salts are used, under normal pressure; in the absence of a base or preferably, where acid salts of hydroxylamine are used, with neutralization of the acid with a base, especially with a hydroxide, such as an alkali metal hydroxide, for example sodium or potassium hydroxide, with a carbonate or hydrogen carbonate, especially an alkali metal or alkaline earth metal carbonate or hydrogen carbonate, for example sodium carbonate, potassium carbonate, sodium hydrogen carbonate, potassium hydrogen carbonate or barium carbonate, with a salt of a weak organic acid, especially an alkali metal or alkaline earth metal salt of a lower alkane-carboxylic acid, for example sodium acetate or potassium acetate, with organic nitrogen bases, especially a secondary or tertiary amine, for example a cyclic 5- or 6-membered secondary or tertiary amine, such as pyrrolidine or pyridine, or with alcoholates, for example alkali metal lower alkyl alcoholates, such as sodium or potassium methanolate, ethanolate or tert-butanolate, or with an anion exchanger, the presence of an alkali metal carbonate being especially preferred; the corresponding compound of formula IV being obtained. Preferably, one of the mentioned salts of hydroxylamine, especially the salt of a hydrohalic acid, such as the hydrochloride salt, is reacted in the mentioned organic solvents, especially in an alcohol, such as methanol or ethanol, at the mentioned temperatures, especially at approximately from 75° to 80° C., to yield the corresponding oxime of formula IV, which can be purified or is used further directly.

N-Hydroxyamidino compounds of formula IV ($R_1$=OH) can be prepared, for example, by reaction of an imino-(lower) alkyl ester derivative or an imino-(lower) alkanethiol ester derivative of a compound of formula VII (in salt form), wherein $W_2$ and $W_3$ together are oxo (preparation as described above), or preferably directly by reaction of a compound of formula VII with hydroxylamine or with a salt thereof, compounds of formula I containing an amidino group ($R_1$=H) being obtained—the reaction is carried out under conditions analogous to those described above for the conversion of compounds of formula VI into compounds of formula IV. Both the cyano group and the carbonyl group in the starting material of formula VII are reacted.

Finally, a compound of formula IV wherein $R_1$ is hydrogen or hydroxy and the other radicals are as defined can be obtained from a compound of formula VII wherein $W_2$ and $W_3$ together are oxo by first reacting the carbonyl group with hydroxylamine, or with a salt thereof, under conditions analogous to those mentioned above for the reaction of compounds of formula VI to form compounds of formula VII, preferably omitting the mentioned bases, there being obtained a compound of formula VII wherein $W_2$ and $W_3$ together are hydroxyimino and the other radicals are as defined above for the corresponding starting material under process a), and then (if desired after isolating the resulting compound of formula VII) reacting the cyano group, under conditions analogous to those described for the reaction of cyano compounds of formula II ($W_1$=cyano) under process a), with ammonia or hydroxylamine or a salt thereof, preferably in the presence of alcoholates, for example alkali metal lower alkyl alcoholates, such as sodium or potassium methanolate, ethanolate or tert-butanolate, in the corresponding alcohols, for example methanol, ethanol or tert-butanol, at preferred temperatures of from 0° C. to the reflux temperature, especially from room temperature to the reflux temperature.

Process c) - Formation of a Schiff's base by reaction of a carbonyl derivative with an amino compound In compounds of formulae V and VI, functional groups that are not intended to participate in the reaction may, if necessary, be in protected form; protecting groups, processes for their introduction and processes for their removal from resulting protected compounds of formula I are analogous to those mentioned in the detailed description of process a).

Reactive derivatives of compounds of formula VI are especially compounds in which there is present instead of the carbonyl function in formula I functionally modified or protected carbonyl in the form of di-lower alkoxymethylene, $C_1$–$C_2$alkylenedioxymethylene, di-lower alkylthiomethylene or $C_1$–$C_2$alkylenedithiomethylene.

The reaction between compounds of formula VI (oxo compound), or their reactive derivatives, and compounds of formula V (aminoimidazole) takes place under conditions that are knownper se, the aminoimidazole of formula V preferably being used in an approximately equimolar amount or in excess relative to the molar amount of the compound of formula VI, especially in an amount that is from 0.95 times to twice the molar amount—in particular, the reaction takes place under conditions that are customary for the reaction of carbonyl compounds with nitrogen bases; preferably in the presence of acids, for example of a hydrohalic acid, such as hydrogen fluoride, hydrogen chloride, hydrogen bromide or hydrogen iodide, especially hydrogen chloride, of sulfuric acid or a hydrogen sulfate, such as an alkali metal hydrogen sulfate, for example sodium hydrogen sulfate, of phosphoric acid, a hydrogen phosphate or a dihydrogen phosphate, for example an alkali metal hydrogen phosphate or dihydrogen phosphate, such as sodium hydrogen phosphate, disodium hydrogen phosphate, potassium hydrogen phosphate or dipotassium hydrogen phosphate, or of an organic acid, especially a carboxylic acid, such as a lower alkanecarboxylic acid that is unsubstituted or substituted in the lower alkyl moiety, preferably by halogen, such as fluorine, chlorine or iodine, for example acetic acid, chloroacetic acid, dichloroacetic acid or trifluoro- or trichloro-acetic acid, of lactic acid or of a sulfonic acid, such as a lower alkanesulfonic acid, for example methanesulfonic acid, ethanesulfonic acid or ethanedisulfonic acid, or an arylsulfonic acid, such as benzene- or naphthalene-sulfonic acid or naphthalene-1,5-disulfonic acid; there being used especially a strong acid, such as sulfuric acid or, more especially, one of the mentioned hydrohalic acids or methanesulfonic acid; in water (in the presence or absence of surfactants) or an aqueous solvent mixture, such as a mixture of water with one or more alcohols, for example methanol, ethanol or, especially, isopropanol, or also di-lower alkyl sulfoxides, such as dimethyl sulfoxide, or di-lower alkyl-lower alkanoylamides, such as dimethylformamide, organic solvents, such as one or more alcohols, for example methanol or ethanol, di-lower alkyl sulfoxides, such as dimethyl sulfoxide, di-lower alkyl-lower alkanoylamides, such as dimethylformamide, or in sufficiently inert nitrites, such as acetonitrile, a mixture of such organic solvents, preferably in an aqueous-alcoholic solution, such as in water/methanol, water/ethanol or, especially, water/isopropanol; preferably at temperatures of from −20° C. to the reflux temperature of the reaction mixture, especially at temperatures of from room temperature to the reflux temperature of the reaction mixture, more especially at approximately from 80° C. to the reflux temperature; the compound of formula I (where appropriate after customary working up) being obtained directly in free form or, especially, in the form of a salt, preferably of the acid present in the reaction, for example in crystalline form. Special preference is given to the reaction of the oxo compound of formula VI and the aminoimidazole of formula V with aqueous HCl in isopropanol at temperatures of from 80° C. to the reflux temperature (for example not higher than 120° C.).

The corresponding reactive derivatives can be prepared from the oxo compounds of formula VI under customary conditions for the preparation of ketals, acetals, thioketals or thioacetals.

The preparation of starting materials of formula VI from corresponding compounds of formula VII has already been described in connection with the preparation of starting materials for process b).

The preparation of the starting materials of formula V has already been described in connection with the preparation of starting materials for process a).

Additional process measures

In the additional process measures, which are carried out if desired, functional groups in the starting materials that are not intended to participate in the reaction may be unprotected or in protected form, for example protected by one or more of the protecting groups mentioned above for process a). Some or all of the protecting groups may be introduced and/or removed by one of the methods mentioned for process a).

The conversion of a compound of formula I wherein $R_1$ is hydroxy and the other radicals each have one of the meanings given, into a different compound of formula I wherein $R_1$ is hydrogen is effected by means of reduction, especially by selective hydrogenation. The selective hydrogenation takes place in the presence of a catalyst and to acid. There are used as catalyst(s) especially cobalt and, more especially, nickel, which is/are employed preferably as such or in finely dispersed form on carriers, such as argillaceous earth, pumice, aluminum oxide, silica gel or activated carbon, with Raney nickel being very especially preferred. There are used as acids especially the acids mentioned above in the definition of salts, which acids are employed in at least an equimolar amount relative to the starting material of formula I in question or in excess, especially in the amount that is stoichiometrically necessary for salt formation with the basic centers of the compounds of formula I; there being used as solvents organic solvents, such as alcohols that are inert under the reaction conditions. for example methanol, ethanol or isopropanol, ethers, such as diethyl ether, dioxane, tetrahydrofuran or anisole, esters, such as ethyl acetate, or, if the acid is an organic acid that is liquid under the reaction conditions, that acid itself, for example acetic acid, mixtures of those solvents, mixtures of water-soluble organic solvents, such as the mentioned alcohols or liquid organic acids, with water, or water itself, of which solvents water, methanol or mixtures thereof are very especially preferred; the reaction temperature being from 0° C. to the reflux temperature of the reaction mixture, especially from 10° to 70° C., for example from approximately 20° C. to approximately 55° C., and the reaction being carried out under slightly reduced pressure, normal pressure or slightly elevated pressure, preferably at from 0.5 to 10 bar, especially the prevailing air pressure, with the introduction of hydrogen, preferably until the calculated amount of hydrogen has been absorbed, especially until the absorption of hydrogen ceases by itself under the reaction conditions. Special preference is given to hydrogenation with hydrogen in the presence of Raney nickel in methanol, water or mixtures thereof, under normal pressure and at temperatures of from 20° to 55° C.

The hydrogenation can also be carried out continuously, for example by allowing solutions of a starting material of formula I wherein $R_1$ is hydroxy to flow over fixed catalysts and bringing those solutions into contact with hydrogen flowing the same way or in the opposite direction, under the above-mentioned conditions.

Salts can be converted into the free compounds in customary manner; metal salts and ammonium salts are converted, for example, by treatment with suitable acids or acid ion exchangers, and acid addition salts are converted, for example, by treatment with a suitable basic agent or basic ion exchangers.

Salts of free compounds of formula I having at least one salt-forming group can be prepared in a manner known per se. For example, salts of compounds of formula I having acidic groups can be formed, for example, by treatment with metal compounds, such as alkali metal salts of suitable organic carboxylic acids, for example the sodium salt of 2-ethyl-hexanoic acid, with inorganic alkali metal or alkaline earth metal compounds, such as the corresponding hydroxides, carbonates or hydrogen carbonates, such as sodium and potassium hydroxide, carbonate or hydrogen carbonate, with corresponding calcium compounds or with ammonia or a suitable organic amine, there preferably being used stoichiometric amounts or only a slight excess of the salt-forming agent. Acid addition salts of compounds of formula I are obtained in customary manner, for example by treatment with an acid or with a suitable anion exchange reagent. Internal salts of compounds of formula I, which contain acidic and basic salt-forming groups, for example a free carboxy group and a free amino group, can be formed, for example, by neutralization of salts, such as acid addition salts, to the isoelectric point, for example with weak bases, or by treatment with ion exchangers.

Isomeric mixtures of compounds of formula I, that is to say mixtures of diastereoisomers and/or enantiomers, for example racemic mixtures, can be separated into the corresponding isomers in a manner known per se by suitable methods of separation. For example, diastereoisomeric mixtures can be separated into the individual diastereoisomers by fractional crystallization, chromatography, solvent partitioning or other customary methods. Racemates can be separated from one another after conversion of the optical antipodes into diastereoisomers, for example by reaction with optically active compounds, for example with optically active acids or bases by the formation of salts with optically pure salt-forming reagents, and separation of the diastereoisomeric mixture so obtainable, for example by means of fractional crystallization; by chromatography on column materials charged with optically active compounds; or by enzymatic methods, for example by selective reaction of only one of the two enantiomers. The separation may be effected either at the stage of one of the starting materials or with the compounds of formula I themselves.

General process conditions

All the above-mentioned process steps can be carried out under reaction conditions that are known per se, preferably those mentioned specifically, in the absence or, customarily, in the presence of solvents or diluents, preferably solvents or diluents that are inert towards the reagents used and are solvents therefor, in the absence or presence of catalysts, condensation agents or neutralizing agents, for example ion exchangers, such as cation exchangers, e.g. in the $H^+$ form, depending on the nature of the reaction and/or of the reactants at reduced, normal or elevated temperature, for example in a temperature range of from approximately −100° C. to approximately 190° C., preferably from approximately −80° C. to approximately 150° C., for example at from −80° to −60° C., at from −20° to 40° C., for example at room temperature, or at the reflux temperature, under atmospheric pressure or in a closed vessel, where appropriate under reduced or elevated pressure, in an inert atmosphere, for example under an argon or nitrogen atmosphere, and/or with the exclusion of light.

At all stages of the reactions, mixtures of isomers that are formed can, if desired, be separated into the individual isomers, for example diastereoisomers or enantiomers, or into any desired mixtures of isomers, for example racemates or mixtures of diastereoisomers, for example analogously to the methods described under "Additional process measures".

The solvents from which those solvents that are suitable for any particular reaction may be selected include, for example, water, esters, such as lower alkyl lower alkanoates, for example ethyl acetate, ethers, such as aliphatic ethers, for example diethyl ether or 1,2-di-methoxyethane, or cyclic ethers, for example tetrahydrofuran, liquid aromatic hydrocarbons, such as benzene, toluene or o-, m- or p-xylene, liquid acyclic hydrocarbons, such as hexane or heptane, alcohols, such as methanol, ethanol, 1- or 2-propanol or diethylene glycol, nitrites, such as acetonitrile, halogenated hydrocarbons, such as methylene chloride or chloroform, acid amides, such as dimethylformamide or dimethylacetamide, ketones, such as lower alkanones, for example acetone, heterocyclic solvents, for example bases, such as heterocyclic nitrogen bases, for example pyridine, or 1,3-dimethyl-3,4,5,6-tetra-hydro-2(1H)-pyrimidone (DMPU), carboxylic acids, such as acetic acid or formic acid, carboxylic acid anhydrides, such as lower alkanoic acid anhydrides, for example acetic anhydride, cyclic, linear or branched hydrocarbons, such as cyclohexane, hexane or iso-pentane, or mixtures of those solvents, for example aqueous solutions, unless otherwise indicated in the description of the processes. Such solvents, or mixtures thereof, may also be used in working up, for example by chromatography or partitioning.

The compounds, including their salts, may also be obtained in the form of hydrates, or their crystals may, for example, include the solvent used for crystallization.

Working up after reactions is carried out, if desired, in accordance with methods known per se, preferably analogously to the methods described in the Examples.

Many of the starting materials mentioned are already known or can be prepared in accordance with processes known per se, for example as described in European Patent Application EP 0 538 193 (published on 21st Apr. 1993), in European Patent Application EP 0 456 133 (published on 13th Nov. 1991) or in Hungarian Patent Application HU 93 02416 (published on 28th Jun. 1994).

The invention relates also to those forms of the process in which a compound obtainable as intermediate at any stage of the process is used as starting material and the remaining process steps are carried out, or in which a starting material is formed under the reaction conditions or is used in the form of a derivative, for example in protected form or in the form of a salt, or a compound obtainable by the process according to the invention, or a salt thereof, is produced under the process conditions and processed further in situ. In the process of the present invention there are preferably used those starting materials which result in the compounds described at the beginning as being especially valuable. Special preference is given to reaction conditions that are analogous to those mentioned in the Examples.

If necessary or desired, protected starting materials can be used in all process steps and the protecting groups can be removed at suitable stages of the reaction.

Protecting groups, the introduction and the freeing thereof are as described in process a).

In view of the close relationship between the compounds of formula I and their starting materials in free form and in the form of salts, any reference hereinbefore and hereinafter to the free compounds and starting materials or their salts is to be understood as meaning also the corresponding salts or free compounds and starting materials, respectively, where appropriate and expedient.

Pharmaceutical processes and compositions

The present invention relates also to pharmaceutical compositions that comprise one of the pharmacologically active compounds of formula I as active ingredient. Compositions for enteral, especially oral, and parenteral administration are especially preferred. The compositions comprise the active ingredient on its own or, preferably, together with a pharmaceutically acceptable carrier. The dose of active ingredient depends upon the disease to be treated, the species, age, weight and individual condition of the individual to be treated, and the mode of administration.

The pharmaceutical compositions comprise from approximately 0.1% to approximately 95% active ingredient, dosage forms that are in single dose form preferably comprising from approximately 1% to approximately 90% active ingredient, and dosage forms that are not in single dose form preferably comprising from approximately 0.1% to approximately 20% active ingredient. Unit dose forms, such as dragées, tablets or capsules, comprise from approximately 1 mg to approximately 500 mg of active ingredient.

The pharmaceutical compositions of the present invention are prepared in a manner known per se, for example by means of conventional mixing, granulating, confectioning, dissolving or lyophilizing processes. For example, pharmaceutical compositions for oral administration can be obtained by combining the active ingredient with one or more solid carriers, optionally granulating a resulting mixture, and, if desired, processing the mixture or granules, if appropriate by the addition of additional excipients, to form tablets or dragée cores.

Suitable carriers are especially fillers, such as sugars, for example lactose, saccharose, mannitol or sorbitol, cellulose preparations and/or calcium phosphates, for example tricalcium phosphate or calcium hydrogen phosphate, and also binders, such as starches, for example corn, wheat, rice or potato starch, methylcellulose, hydroxypropylmethylcellulose, sodium carboxymethylcellulose and/or polyvinylpyrrolidone, and/or, if desired, disintegrators, such as the above-mentioned starches and also carboxymethyl starch, cross-linked polyvinylpyrrolidone, or alginic acid or a salt thereof, such as sodium alginate.

Additional excipients are especially flow conditioners and lubricants, for example silicic acid, talc, stearic acid or salts thereof, such as magnesium or calcium stearate, and/or polyethylene glycol, or derivatives thereof.

Dragée cores can be provided with suitable, optionally enteric, coatings, there being used inter alia concentrated sugar solutions, which may comprise gum arabic, talc, polyvinyl-pyrrolidone, polyethylene glycol and/or titanium dioxide, or coating solutions in suitable organic solvents or solvent mixtures or, for the preparation of enteric coatings, solutions of suitable cellulose preparations, such as acetylcellulose phthalate or hydroxypropylmethylcellulose phthalate. Colorings or pigments may be added to the tablets or dragée coatings, for example for identification purposes or to indicate different doses of active ingredient.

Pharmaceutical compositions for oral administration are also hard gelatin capsules, and soft sealed capsules consisting of gelatin and a plasticizer, such as glycerol or sorbitol. The hard gelatin capsules may contain the active ingredient in the form of granules, for example in admixture with fillers, such as corn starch, binders and/or glidants, such as talc or magnesium stearate, and, where appropriate, stabilizers. In soft capsules the active ingredient is preferably dissolved or suspended in suitable liquid excipients, for example fatty oils, paraffin oil or liquid polyethylene glycols, it likewise being possible to add stabilizers.

Other oral dosage forms are, for example, syrups prepared in customary manner which comprise the active ingredient, for example, in dispersed form and in a concentration of approximately from 0.1% to 10%, preferably approximately 1% or in a similar concentration that provides a suitable single dose when administered, for example, in a measure of 5 or 10 ml. Also suitable are, for example, powdered or liquid concentrates for the preparation of shakes, for example in milk. Such concentrates may also be packaged in single dose quantities Suitable rectally administrable pharmaceutical compositions are, for example, suppositories that consist of a combination of the active ingredient with a suppository base. Suitable suppository bases are, for example, natural or synthetic triglycerides, paraffin hydrocarbons, polyethylene glycols or higher alkanols.

For parenteral administration there are suitable, especially, aqueous solutions (preferably in the presence of sodium chloride) of an active ingredient in water-soluble form, for example in the form of a water-soluble salt, or aqueous injection suspensions that comprise viscosity-increasing substances, for example sodium carboxymethylcellulose, sorbitol and/or dextran, and, if desired, stabilizers. The active ingredient, where appropriate together with excipients, can also be in the form of a lyophilisate and be made into a solution prior to parenteral administration by the addition of suitable solvents.

Solutions of the kind used, for example, for parenteral administration can also be used as infusion solutions.

The invention relates also to pharmaceutical compositions and to a method for the (therapeutic or prophylactic) treatment of the above-mentioned diseases, for example of tumors, metastases or protozoal diseases, an amount of a compound of formula I according to the invention that is prophylactically, or preferably, therapeutically effective against the mentioned diseases being present in a pharmaceutical composition that is suitable for administration to a warm-blooded animal, especially a human, requiring that treatment for the treatment of one of the mentioned diseases; and a therapeutically effective amount of a compound of formula I according to the invention being administered in the treatment method to a warm-blooded animal, for example a human, requiring such treatment on account of one of the mentioned diseases, in an amount that is prophylactically or therapeutically effective against that disease.

The invention relates also to a method of treating the above-mentioned pathological conditions.

Accordingly, the compounds of the present invention can be administered prophylactically or therapeutically, preferably in the form of pharmaceutical compositions. For a body weight of approximately 70 kg, a daily dose of from approximately 1 mg to approximately 1000 mg, preferably of approximately from 25 to 100 mg orally. and from 2 to 50 mg parenterally, of a compound of the present invention is administered. Children usually receive half the adult dose.

The following Examples serve to illustrate the invention, but do not limit the scope thereof in any way.

Temperatures are given in degrees Celsius.

The following abbreviations are used: DMF=N,N-dimethylformamide; DMSO=dimethyl sulfoxide; MS (FAB) =mass spectrum (fast atom bombardment).

N-Hydroxyamidino is the group —C(=NOH)—$NH_2$. 4-Tolyl is the p-methylphenyl radical.

EXAMPLE 1

1-[4-(N-Hydroxyamidino)-2,3-dihydro-1H-inden-1-ylideneamino]-2-amino-4-phenyl-imidazole dihydrochloride 6 ml of 32% hydrochloric acid (Merck, Darmstadt, Germany; p.a.) are added, with stirring, to a mixture of 4.1 g (0.02 mol) of 4-(N-hydroxyamidino)-2,3-dihydro-1H-inden-1-one oxime, 3.5 g (0.02 mol) of 1,2-diamino-4-phenyl-imidazole (see Beyer H. et al., Chem. Ber. 101, 3151 (1968)) and 150 ml of isopropanol, and the mixture is stirred at 80° C. for 5 hours. During that time, the starting materials dissolve and the title compound gradually crystallizes out. At the end of the reaction time, the mixture is cooled. The product that has crystallized out is filtered off with suction, washed with isopropanol and dried. The product crystallizes with one mole of isopropanol, m.p. 238°–240° C., $^1$H-NMR (DMSO/$D_2O$): δ=8.24 (d, 1H); 7.88 (s, 1H); 7.73 (d, 1H); 7.55–7.68 (m, 3H); 7.34–7.5 (m, 3H); 3.26 (s, 4H).

(For another method of synthesis, see Example 32).

The starting material is prepared as follows:

a) 4-(N-Hydroxyamidino)-2,3-dihydro-1H-inden-1-one oxime

Variant 1:

A mixture of 20.43 g (0.13 mol) of 4-cyano-2,3-dihydro-1H-inden-1-one [Coll. Czechoslov. Chem. Commun. 43, 3227 (1978)], 18.07 g (0.26 mol) of hydroxylamine hydrochloride, 13.46 g (0.127 mol) of sodium carbonate and 650 ml of 50% aqueous ethanol is stirred at 800 for 3.5 h6urs. A further 9.035 g (0.13 mol) of hydroxylamine hydrochloride and 6.73 g (0.0635 mol) of sodium carbonate are then added to the reaction mixture, stirring is continued at 80° for a further 5 hours, and the reaction mixture is allowed to cool slowly to room temperature. The reaction mixture is then cooled to 10° and is filtered, and the resulting product is washed with 20 ml of 50% aqueous ethanol and a small amount of diethyl ether. The crystallizate is then added to 900 ml of methanol, the mixture is stirred at room temperature for one hour, insoluble constituents are filtered off, and the filtrate is concentrated to a volume of approximately 150 ml. The product precipitated on cooling to 5° C. is filtered off, washed with a small amount of methanol and diethyl ether, and dried. The title compound so obtained melts at 192°–194° (decomp.).

Variant 2:

10.4 g (150 mmol) of hydroxylamine hydrochloride and 37.5 ml of 2M $Na_2CO_3$ solution are added, with stirring, to a solution of 7.86 g (50 mmol) of 4-cyano-2,3-dihydro-1H-inden-1-one [Coll. Czechoslov. Chem. Commun. 43 3227 (1978)] in 75 ml of N,N-dimethylformamide, and the reaction mixture is heated at 75° C. for 3.75 hours. While still warm, the reaction mixture is diluted with 25 ml of water and is filtered while warm. 88 ml of water are then added to the filtrate, with stirring, and the mixture is cooled to 0°–5° C. The product that has crystallized out is filtered off with suction, is washed with DMF/water 1:3 and finally with ethanol, is dried and is recrystallized from three times the amount of DMF. In that manner there is obtained the title compound, which melts at 192°–194° (decomp.); MS (FAB): (M+H)$^+$=206; $^1$H-NMR (DMSO): δ=10.87 (s, 1H); 9.64 (s, 1H); 7.56 (d, 1H); 7.49 (d, 1H); 7.30 (t, 1H); 5.76 (s, 2H); 3.15 (t, 2H); 2.74 (t, 2H).

Variant 3:

A mixture of 157 mg (1.0 mmol) of 4-cyano-2,3-dihydro-1H-inden-1-one [Coll. Czechoslov. Chem. Commun. 43, 3227 (1978)] and 139 mg (2.0 mmol) of hydroxylamine hydrochloride in 4 ml of ethanol is stirred at 80° C. for 1.5 hours and cooled in an ice-water bath. The product that has crystallized out is filtered off with suction, washed with cold ethanol and diethyl ether and dried. In that manner there is obtained the intermediate 4-cyano-2,3-dihydro-1H-inden-1-one oxime, which melts at 200°–202° C. with decomposition; $^1$H-NMR (DMSO): δ=11.22 (s, 1H); 7.84 (d, 1H); 7.81 (d, 1H); 7.45 (t, 1H); 3.15 (t, 2H); 2.84 (t, 2H).

920 mg (5.1 mmol) of sodium methanolate are added to a mixture of 360 mg (2.06 mmol) of the intermediate 4-cyano-2,3-dihydro-1H-inden-1-one oxime and 355 mg (5.1 mmol) of hydroxylamine hydrochloride in 10 ml of methanol, and the reaction mixture is stirred at room temperature for 10 minutes. The reaction mixture is then filtered and the filtrate is boiled under reflux conditions for 2 hours. After cooling, the resulting product is filtered off, washed with a small amount of methanol and dried. In that manner there is obtained the title compound, which melts at 192°–194° (decomp.); $^1$H-NMR (DMSO): δ=10.87 (s, 1H); 9.64 (s, 1H); 7.56 (d, iH); 7.49 (d, 1H); 7.30 (t, 1H); 5.76 (s, 2H); 3.15 (t, 2H); 2.74 (t, 2H).

EXAMPLE 2:

1-[4-(Amidino)-2,3-dihydro-1H-inden-1: -ylideneamino]-2-amino-4-phenyl-imidazole dihydrochloride 0.2 g of Raney nickel is added to a solution of 2.0 g (0.0048 mol) of 1-[4-(N-hydroxy-amidino)-2,3-dihydro-1H-inden-1-ylideneamino]-2-amino-4-phenyl-imidazole dihydrochloride in 100 ml of methanol, and hydrogenation is carried out at room temperature and under normal pressure until the absorption of hydrogen has ceased. The reaction mixture is then filtered and the catalyst is washed thoroughly with methanol. The filtrate is adjusted to pH 4 with a small amount of 2N alcoholic hydrochloric acid and is concentrated. The product that has crystallized out is filtered off with suction and recrystallized from 30 ml of methanol, yielding the title compound in the form of the trihydrate, m.p. 211°–215° C., $^1$H-NMR (DMSO): δ=9.56 (d, 4H); 8.34 (d, 1H); 8.14 (s, 1H); 7.97 (s, 2H); 7.82 (m, 3H); 7.67 (t, 1H); 7.3–7.52 (m, 4H); 3.41 (s, 4H).

EXAMPLE 3

1-[4-(N-Hydroxyamidino)-2,3-dihydro-1H-inden-1-ylideneamino]-2-amino-4-(4-methoxvphenyl)-imidazole dihydrochloride 7.2 ml of 32% hydrochloric acid (Merck, Darmstadt, Germany; p.a.) are added, with stirring, to a mixture of 4.92 g (0.024 mol) of 4-(N-hydroxyamidino)-2,3-dihydro-1H-inden-1-one oxime, 4.9 g (0.024 mol) of 1,2-diamino-4-(4-methoxyphenyl)-imidazole (see Hetzheim A. et al., Chem. Ber. 100, 3418 (1967)) and 120 ml of isopropanol, and the reaction mixture is stirred at 80° C. for 19 hours. The reaction mixture is filtered while hot and the filtrate is cooled. The pale-yellow title product that has crystallised out is filtered off with suction and dried. It crystallizes in the form of the monohydrate, m.p. >220° C., MS (FAB): (M+H)$^+$=377, $^1$H-NMR (DMSO/D$_2$O): δ=8.23 (d, 1H); 7.74 (s, 1H); 7.72 (d, 1H); 7.57–7.63 (m, 3H); 7.02 (d, 2H); 3.75 (s, 3H), 3.26 (s, 4H).

EXAMPLE 4

1-[4-(Amidino)-2,3-dihydro-1H-inden-1-ylideneamino]-2-amino-4-(4-methoxvphenyl)-imidazole dihydrochloride Analogously to Example 2, approximately 2 g of Raney nickel are added to a solution of 5.8 g (0.00129 mol) of 1-[4-(N-hydroxyamidino)-2,3-dihydro-1H-inden-1-ylideneamino]-2-amino-4-(4-methoxyphenyl)-imidazole dihydrochloride in 600 ml of methanol, and hydrogenation is carried out at room temperature and under normal pressure until the absorption of hydrogen has ceased. The reaction mixture is then filtered and the filtrate is concentrated. The product that has crystallised out is filtered off with suction and recrystallized from methanol, yielding the title compound in the form of the monohydrate, m.p. >220° C., $^1$H-NMR (DMSO): δ=9.56 (d, 4H); 8.33 (d, 1H); 7.99 (s, 1H); 7.94 (s, 2H); 7.75–7.84 (m, 3H); 7.64 (t, 1H); 7.04 (d, 2H); 3.80 (s, 3H), 3.40 (m, 4H).

EXAMPLE 5

1-[4-(N-Hydroxyamidino)-2,3-dihydro-1H-inden-11-ylideneamino]-2-amino-4-(2-methoxyphenyl)-imidazole dihydrochloride 0.6 ml of 32 % hydrochloric acid (Merck, Darmstadt, Germany; p.a.) is added, with stirring, to a mixture of 0.41 g (0.002 mol) of 4-(N-hydroxyamidino)-2,3-dihydro-1H-inden-1-one oxime, 0.408 g (0.002 mol) of 1,2-diamino-4-(2-methoxyphenyl)-imidazole and 10 ml of isopropanol, and the reaction mixture is stirred at 80° C. for 20 hours. The reaction mixture is filtered while hot and the filtration product is washed with isopropanol and dried. In that manner there is obtained the title compound, m.p. >220° C., $^1$H-NMR (DMSO/D$_2$O): δ=8.22 (d, 1H); 7.77 (m, 2H); 7.58 (m, 2H); 7.36 (m, 1H); 7.12 (d, 1H); 7.05 (t, 1H); 3.88 (s, 3H), 3.24 (s, 4H).

The starting materials are prepared as follows:

a) 2-Amino-1-benzylideneamino-4-(2-methoxyphenyl)-imidazole

A solution of 41.7 g (0.257 mol) of benzaldehyde guanylhydrazone (see Thiele, A., Liebigs Annalen der Chemie 270, 35) and 30.12 g of 2-methoxyphenacyl bromide (Aldrich, Buchs, Switzerland; 98%, Cat. no. 10,085-4) in 130 ml of ethanol is boiled under reflux for one hour. After cooling, the product that has crystallised out is filtered off with suction and recrystallized from ethanol. In that manner there is obtained the title compound, m.p. 166°–167° C., $^1$H-NMR (DMSO): δ=8.61 (s, 1H); 8.0 (m, 3H); 7.88 (s, 1H); 7.5 (m, 3H); 7.19 (m, 1H); 7.03 (d, 1H); 6.96 (t, 1H); 6.16 (s, 2H); 3.94 (s, 3H).

b) 1,2-Diamino-4-(2-methoxyphenyl)-imidazole

A solution of 23.2 g of 2-amino-1-benzylideneamino-4-(2-methoxyphenyl)-imidazole and 15.8 ml of hydrazine hydrate in 80 ml of diethylene glycol is stirred at 170° C. for 7 hours. After cooling, 400 ml of water are added to the reaction mixture. The product that has separated out is filtered off with suction, washed with water and recrystallized from 200 ml of ethanol. In that manner there is obtained the title compound, m.p. 195°–196° C., $^1$H-NMR (DMSO): δ=7.9 (d, 1H); 7.06 (m, 2H); 6.91 (m, 2H); 5.52 (s, 2H); 5.3 (s, 2H); 3.88 (s, 3H).

EXAMPLE 6

1-[4-(Armidino)-2,3-dihydro-1H-inden-1-ylideneamino]-2-amino-4-(2-methoxyphenyl)-imidazole dihydrochloride Analogously to Example 2, approximately 0.2 g of Raney nickel is added to a solution of 0.45 g (0.001 mol) of 1-[4-(N-hydroxyamidino)-2,3-dihydro-1H-inden-1-ylideneamino]-2-amino-4-(2-methoxyphenyl)-imidazole dihydrochloride in 50 ml of methanol/water 1:1, and hydrogenation is carried out at room temperature and under normal pressure until the absorption of hydrogen has ceased. The reaction mixture is then diluted with 100 ml of methanol and filtered. The filtrate is adjusted to pH 4 with a small amount of 2N alcoholic hydrochloric acid and is concentrated to dryness by evaporation. The residue is recrystallized from ethyl acetate, yielding the title compound in the form of the dihydrate, m.p. >220° C. (decomp.), $^1$H-NMR (DMSO/D$_2$O): δ=8.28 (d, 1H); 7.80 (m, 2H); 7.64 (m, 2H); 7.38 (t, 1H); 7.16 (d, 1H); 7.06 (t, 1H); 3.91 (s, 3H), 3.30 (m, 4H).

EXAMPLE 7

1-[4-(N-Hydroxyamidino)-2,3-dihydro-1H-inden-1-ylideneamino]-2-amino-4-(2,5-dimethoxyphenyl)-imidazole dihydrochloride 0.6 ml of concentrated hydrochloric acid is added, with stirring, to a mixture of 0.41 g (0.002 mol) of 4-(N-hydroxyamidino)-2,3-dihydro-1H-inden-1-one oxime, 0.47 g (0.002 mol) of 1,2-diamino-4-(2,5-dimethoxyphenyl)-imidazole and 10 ml of isopropanol, and the reaction mixture is stirred at 80° C. for 3.hours. The reaction mixture is filtered while hot and the filtration product is washed with isopropanol and dried. In that manner there is obtained the title compound, m.p. >220° C., $^1$H-NMR (DMSO/D$_2$O): δ=8.23 (d, 1H); 7.75 (m, 2H); 7.61 (t, 1H); 7.17 (d, 1H); 7.07 (d, 1H); 6.93 (q, 1H); 3.82 (s, 3H), 3.71 (s, 3H); 3.25 (bs, 4H).

The starting materials are prepared as follows:

a) 2-Amino-1-benzylideneamino-4-(2,5-dimethoxyphenyl)-imidazole

A solution of 1.62 g (0.01 mol) of benzaldehyde guanylhydrazone and 1.34 g of 2,5-dimethoxyphenacyl bromide (Aldrich, Buchs, Switzerland, 97%, Cat. no. 10,458-2) in 5 ml of ethanol is boiled under reflux for 45 minutes. After cooling, the product that has crystallized out is filtered off with suction and recrystallized from ethanol. In that manner there is obtained the title compound, m.p. 180°–181° C., $^1$H-NMR (DMSO): δ=8.62 (s, 1H); 7.97 (m, 2H); 7.90 (s, 1H); 7.42–7.60 (m, 4H); 6.95 (d, 1H); 6.76 (m, 1H); 6.18 (s, 2H); 3.9 (s, 3H); 3.73 (s, 3H).

b) 1.2-Diamino-4-(2,5-dimethoxyphenyl)-imidazole

A solution of 26.1 g of 2-amino-1-benzylideneamino-4-(2,5-dimethoxyphenyl)-imidazole and 16.2 ml of hydrazine hydrate in 80 ml of diethylene glycol is stirred at 170° C. for 6 hours. After cooling, 400 ml of water are added to the reaction mixture. The product that has separated out is filtered off with suction, washed with water and recrystallized from 150 ml of ethanol. In that manner there is obtained the title compound, m.p. 159°–160° C., $^1$H-NMR (DMSO): δ=7.47 (d, 1H); 7.07 (s, 1H); 6.87 (d, 1H); 6.63 (q, 1H); 5.52 (s, 2H); 5.34 (s, 2H); 3.79 (s, 3H); 3.69 (s, 3H).

EXAMPLE 8

1-[4-(Amidino)-213-dihydro-1H-inden-1-ylideneamino]-2-amino-4-(2,5-di-methoxyphenyl)-imidazole dihydrochloride Analogously to Example 2, approximately 0.2 g of Raney nickel is added to a solution of 0.48 g (0.001 mol) of 1-[4-(N-hydroxyamidino)-2,3-dihydro-1H-inden-1-ylideneamino]-2-amino-4-(2,5-dimethoxyphenyl)-imidazole dihydrochloride in 50 ml of methanol/water 1:1, and hydrogenation is carried out at room temperature and under normal pressure until the absorption of hydrogen has ceased. The reaction mixture is then diluted with 100 ml of methanol and filtered. The filtrate is adjusted to pH 4 with a small amount of 2N alcoholic hydrochloric acid and is concentrated in vacuo to approximately 50 ml. The product that has crystallized out, which is filtered off with suction and dried, is the title compound in the form of the dihydrate, m.p. 260° C. (decomp.), $^1$H-NMR (DMSO/D$_2$O): δ=8.27 (d, 1H); 7.82 (m, 2H); 7.64 (t, 1H); 7.28 (d, 1H); 7.09 (d, 1H); 6.94 (q, 1H); 3.76 (s, 3H), 3.30 (m, 4H).

EXAMPLE 9

1-[4-(N-Hydroxvamidino)-2,3-dihydro-1H-inden-1-ylideneamino]-2-amino-4-(3-methoxyphenyl)-imidazole dihydrochloride 6.0 ml of 32% hydrochloric acid (Merck, Darmstadt, Germany; p.a.) are added, with stirring, to a mixture of 4.1 g (0.02 mol) of 4-(N-hydroxyamidino)-2,3-dihydro-1H-inden-1-one oxime, 4.08 g (0.02 mol) of 1,2-diamino-4-(3-methoxyphenyl)-imidazole and 100 ml of isopropanol, and the reaction mixture is stirred at 80° C. for 18 hours. The reaction mixture is filtered while hot and the filtration product is washed with isopropanol and dried. In that manner there is obtained the title compound, m.p. 257°–259° C., $^1$H-NMR (DMSO/D$_2$O): δ=8.24 (d, 1H); 7.91 (s, 1H); 7.75 (d, 1H); 7.61 (t, 1H); 7.38 (t, 1H); 7.25 (m, 2H); 6.95 (m, 1H); 3.76 (s, 3H), 3.27 (s, 4H).

The starting materials are prepared as follows:

a) 2-Amino-1-benzylideneamino-4-(3-methoxyphenyl)-imidazole

A solution of 16.2 g (0.1 mol) of benzaldehyde guanylhydrazone and 11.8 g (0.050 mol) of 3-methoxyphenacyl bromide (Aldrich, Buchs, Switzerland; 98 %, Cat. no. 11,567-3) in 50 ml of ethanol is stirred at 20° C. for 3 hours. The product that has crystallized out is filtered off with suction and dried. In that manner there is obtained the title compound, m.p. 170°–171° C., $^1$H-NMR (DMSO): δ=8.56 (s, 1H); 8.03 (s, 1H); 7.92 (m, 2H); 7.5 (m, 3H); 7.26 (m, 3H); 6.76 (m, 1H); 6.2 (s, 2H); 3.8 (s, 3H).

b) 1,2-Diamino-4-(3-methoxy-phenyl)-imidazole

A solution of 8.1 g of 2-amino-1-benzylideneamino-4-(3-methoxyphenyl)-imidazole and 5.5 ml of hydrazine hydrate in 28 ml of diethylene glycol is stirred at 170° C. for 7 hours. After cooling, 150 ml of water are added to the reaction mixture. The product that has separated out is filtered off with suction, washed with water and recrystallized from 100 ml of ethanol. In that manner there is obtained the title compound, m.p. 181°–182° C., $^1$H-NMR (DMSO): δ=7.17 (m, 3H); 7.06 (s, 1H); 6.64 (m, 1H); 5.52 (s, 2H); 5.35 (s, 2H); 3.74 (s, 3H).

EXAMPLE 10

1-[4-(Amidino)-2,3-dihydro-1 1H-inden- 1-ylideneamino]-2-amino-4-(3-methoxyphenyl)-imidazole dihydrochloride Analogously to Example 2, approximately 2 g of Raney nickel are added to a solution of 4.1 g (0.008 mol) of 1-[4-(N-hydroxyamidino)-2,3-dihydro-1H-inden-1-ylideneamino]-2-amino-4-(3-methoxyphenyl)-imidazole dihydrochloride in 410 ml of water, and hydrogenation is carried out at room temperature and under normal pressure until the absorption of hydrogen has ceased. The reaction mixture is then diluted with 1.3 liters of methanol and filtered. The filtrate is adjusted to pH 4 with a small amount of 2N alcoholic hydrochloric acid and is concentrated in vacuo to approximately 200 ml. The product that has crystallized out, which is filtered off with suction and dried, is the title compound in the form of the monohydrate, m.p. 260° C. (decomp.), $^1$H-NMR (DMSO/D$_2$O): δ=8.32 (d, 1H); 8.05 (s, 1H); 7.83 (d, 1H); 7.65 (t, 1H); 7.3–7.44 (m, 3H); 6.94 (d, 1H); 3.81 (s, 3H); 3.36 (s, 4H).

EXAMPLE 11

1-[4-(N-Hydroxyamidino)-2,3-dihydro-1H-inden-1-ylideneamino]-2-amino-4-(4-chlorophenyl)-imidazole dihydrochloride A mixture of 1.026 g (5 mmol) of 4-(N-hydroxyamidino)-2,3-dihydro-1H-inden-1-one oxime, 1.043 g (5 mmol) of 1,2-diamino-4-(4-chlorophenyl)-imidazole (see Beyer H. et al., Chem. Ber. 101, 3151 (1968)) and 20 ml of 4N hydrochloric acid is heated at 120° C. for 18 hours, with stirring, and is then concentrated by evaporation in vacuo. 25 ml of ethanol are added to the crystalline residue, the mixture is cooled to 5° C., with stirring, and is filtered, and the crystallizate is washed with a small amount of ethanol and diethyl ether. The crude title compound, dried under a high vacuum, contains 8.17% water and melts at 226°–228° C.

(decomp.), $^1$H-NMR (D$_2$O): δ=8.06 (d, 1H); 7.75 (d, 1H); 7.55 (t, 1H); 7.40 (s, 1H); 7.38 (d, 2H); 7.28 (d, 2H); 3.21–3.27 (m, 2H), 3.03–3.09 (m, 2H).

EXAMPLE 12

1-[4-(Amidino)-2,3-dihydro-1H-inden-1-ylideneamino]-2-amino-4-(4-chlorophenyl)-imidazole dihydrochloride Analogously to Example 2, 0.2 g of Raney nickel is added to a solution of 1.0 g (2.024 mmol) of 1-[4-(N-hydroxyamidino)-2,3-dihydro-1H-inden-1-ylideneamino]-2-amino-4-(4-chlorophenyl)-irnidazole dihydrochloride in 35 ml of methanol and 20 ml of water, and hydrogenation is carried out at room temperature and under normal pressure until the absorption of hydrogen has ceased. The reaction mixture is then diluted with 50 ml of methanol and filtered. The filtrate is adjusted to pH 3 with a small amount of 3N methanolic hydrochloric acid and is concentrated to a volume of approximately 30 ml. After cooling in an ice-bath, the product that has crystallized out is filtered off, washed with a small amount of methanol and diethyl ether and dried under a high vacuum at 120° C. The title compound is obtained in the form of the monohydrate, m.p. 245°–250° C. (decomp.), $^1$H-NMR (DMSO/D$_2$O): δ=8.33 (d, 1H); 8.12 (s, 1H); 7.79–7.87 (m, 3H); 7.67 (t, 1H); 7.57 (d, 2H); 3.38 (s, 4H).

EXAMPLE 13

1-[4-(N-Hydroxyamidino)-2,3-dihydro-1H-inden-1-ylideneamino]-2-amino-4-(4-tolyl)-imidazole dihydrochloride A mixture of 1.20 g (5.848 mmol) of 4-(N-hydroxyamidino)-2,3-dihydro-1H-inden-1-one oxime, 1.10 g (5.844 mmol) of 1,2-diamino-4-(4-tolyl)-imidazole (Beyer H. et al., Chem. Ber. 101, 3151 (1968)) and 20 ml of 4N hydrochloric acid is heated at 110° C. for 22 hours, with stirring, and is then concentrated in vacuo to approximately half its original volume. The product that has crystallized out is filtered off, washed with isopropanol and recrystallized from a mixture of 15 ml of methanol and 30 ml of isopropanol, yielding the title compound in the form of the dihydrate, m.p. 225°–232° C. (decomp.), $^1$H-NMR (D$_2$O): δ=8.04 (d, 1H); 7.74 (d, 1H); 7.55 (t, 1H); 7.30 (s, 1H); 7.26 (d, 2H); 7.07 (d, 2H); 3.17–3.23 (m, 2H); 2.98–3.04 (m, 2H); 2.07 (s, 3H).

EXAMPLE 14

1-[4-(Amidino)-2,3-dihydro-1H-inden-1-ylideneamino]-2-amino-4-(4-tolyl)-imidazole dihydrochloride Analogously to Example 2, 0.2 g of Raney nickel is added to a solution of 0.9 g (1.917 mmol) of 1-[4-(N-hydroxyamidino)-2,3-dihydro-1H-inden-1-ylideneamino]-2-amino-4-(4-tolyl)-imidazole dihydrochloride in 60 ml of methanol/water (1:1), and hydrogenation is carried out at room temperature and under normal pressure until the absorption of hydrogen has ceased. The reaction mixture is then filtered, and the filtrate is acidified to pH 3 with 3N methanolic hydrochloric acid and is concentrated to a volume of approximately 20 ml. The product that has crystallized out is filtered off and recrystallized from ethanol/water, yielding the title compound with a water content of 11.81%, m.p. 220°–225° C. (decomp.), $^1$H-NMR (DMSO/D$_2$O): δ=8.33 (d, 1H); 7.98 (s, 1H); 7.83 (d, 1H); 7.61–7.71 (m, 3H); 7.29 (d, 2H); 3.37 (s, 4H); 2.34 (s, 3H).

EXAMPLE 15

1-[4-(N-Hydroxyamidino)-2,3-dihydro-1H-inden-1-ylideneamino]-2-amino-4-(4-fluorophenyl)-imidazole dihydrochloride 1.91 ml of 37% hydrochloric acid are added, with stirring, to a mixture of 1.303 g (6.35 mmol) of 4-(N-hydroxyamidino)-2,3-dihydro-1H-inden-1-one oxime, 1.22 g (6.348 mmol) of 1,2-diamino-4.-(4-fluorophenyl)-imidazole and 32 ml of isopropanol, and the reaction mixture is stirred at 110° C. for 4 hours. Filtration of the hot reaction mixture, washing of the crystallizate with isopropanol and drying under a high vacuum yield the title compound in the form of the monohydrate with an isopropanol content of 4.17%, m.p. 242°–247° C. (decomp.), $^1$H-NMR (D$_2$O): δ=8.12 (d, 1H); 7.79 (d, 1H); 7.52–7.63 (m, 3H); 7.47 (s, 1H); 7.65 (t, 2H); 3.28–3.32 (m, 2H); 3.16–3.20 (m, 2H).

The starting materials are prepared as follows:

a) 2-Amino-1-benzylideneamino-4-(4-fluorophenyl)-imnidazole 7.32 ml (0.0525 mol) of triethyl amine and 8.63 g (0.05 mol) of 2-chloro-4'-fluoro-aceto-phenone (Aldrich, Buchs, Swilzerland; 99%, Cat. no. 13,288-8) are added to a solution of 8.11 g (0.05 mol) of benzaldehyde guanylhydrazone in 40 ml of ethanol. The reaction mixture is stirred at 20° C. for 0.5 hour and is then boiled under reflux for 2.5 hours. After cooling to 5° C., the product that has crystallized out is filtered off, washed with diethyl ether and dried. In that manner there is obtained the title compound, m.p. 207°–210° C., $^1$H-NMR (DMSO): δ=8.55 (s, 1H); 8.00 (s, 1H); 7.90–7.98 (m, 2H); 7.69–7.79 (m, 2H); 7.45–7.57 (m, 3H); 7.15–7.27 (m, 2H); 6.22 (s, 2H).

b) 1,2-Diamino-4-(4-fluorophenyl)-imidazole

A solution of 5.3 g (0.0189 mol) of 2-amino-1-benzylideneamino-4-(4-fluorophenyl)-imidazole and 12.5 ml of hydrazine hydrate in 18.8 ml of diethylene glycol is stirred at 140° C. for 15 hours. After cooling to 80° C., 70 ml of acetonitrile are added to the reaction mixture, which is then cooled further to 0° C. The product that has separated out is filtered off and washed with acetonitrile and diethyl ether. In that manner there is obtained the title compound, m.p. 227°–230° C., $^1$H-NMR (DMSO): δ=7.57–7.68 (m, 2H); 7.06–7.15 (m, 2H); 7.01 (s, 1H); 5.52 (s, 2H); 5.36 (s, 2H).

EXAMPLE 16

1-[4-(Amidino)-2,3-dihydro-1H-inden-1-ylideneamino]-2-amino-4-(4-fluoro-phenyl)-imidazole dihydrochloride Analogously to Example 2, 0.25 g of Raney nickel is added to a solution of 1.0 g (2.105 mmol) of 1-[4-(N-hydroxyamidino)-2,3-dihydro-1H-inden-1-ylideneamino]-2-amino-4-(4-fluorophenyl)-imidazole dihydrochloride in 70 ml of methanol/water (1:1), and hydrogenation is carried out at room temperature and under normal pressure until the absorption of hydrogen has ceased. The reaction mixture is then filtered, the filtrate is acidified to pH 3 with 3N methanolic hydrochloric acid, and concentration is carried out by evaporation in vacuo. The crystalline residue is recrystallized from methanol/diethyl ether, yielding the title compound with a water content of 4.88%, m.p. 245°–250° C. (decomp.), $^1$H-NMR (D$_2$O): δ=8.09 (d, 1H); 7.81 (d, 1H); 7.44–7.61 (m, 3H); 7.42 (s, 1H); 7.03–7.15 (m, 2H); 3.27–3.33 (m, 2H); 3.11–3.17 (m, 2H).

EXAMPLE 17

1-[4-(N-Hydroxyamidino)-2,3-dihydro-1H-inden-1-ylideneamino]-2-amino-4-ethyl-imidazole dihydrochloride 3.2 ml of 32% hydrochloric acid (Merck, Darmstadt, Germany; p.a.) are added, with stirring, to a mixture of 3.28 g (0.016 mol) of 4-(N-hydroxyamidino)-2,3-dihydro-1H- inden-1-one oxime, 2.6 g (0.016 mol) of 1,2-diamino-4-ethyl-imidazole hydrochloride and 150 ml of isopropanol, and the reaction mixture is stirred at 80° C. for 90 hours. The reaction mixture is filtered while hot and the filtration product is washed with isopropanol and dried. In that manner there is obtained the title compound, m.p. 245°–246° C., $^1$H-NMR (DMSO/D$_2$O): δ=8.22 (d, 1H); 7.73 (d, 1H); 7.59 (t, 1H); 7.19 (s, 1H); 3.2 (m, 4H); 2.47 (m, 2H); 1.17 (t, 3H).

The starting materials are prepared as follows:

a) 2-Amino-1-benzylideneamino-4-ethyl-imidazole

A solution of 1.62 g (0.01 mol) of benzaldehyde guanylhydrazone and 0.84 g (0.005 mol) of 1-bromo-2-butanone (Aldrich, Buchs, Switzerland; tech. 90%, Cat. no. 24,329-9) in 5 ml of ethanol is stirred for one hour in an ice-water bath and for 16 hours at 20° C. The reaction mixture is then concentrated to dryness by evaporation. The residue is taken up in lethyl acetate, washed twice with water and once with dilute sodium chloride solution, and dried over MgSO$_4$. The ethyl acetate solution is concentrated, whereupon the title compound crystallizes out, m.p. 164°–167° C., $^1$H-NMR (DMSO): δ=8.41 (s, 1H); 8.89 (m, 2H); 7.46 (m, 3H); 7.13 (s, 1H); 5.9 (s, 2H); 2.34 (q, 2H); 1.13 (t, 3H).

b) 1,2-Diamino-4-ethyl-imidazole hydrochloride

A mixture of 4.29 g (0.02 mol) of 2-amino-1-benzylideneamino-4-ethyl-imidazole and 25 ml of 2N hydrochloric acid is heated to 120° C. and subjected to steam distillation for one hour. The distillation residue is cooled and then concentrated to dryness by evaporation, and the residue is crystallized from ethanol/ethyl acetate. In that manner there is obtained the title compound, m.p. 124°–125° C., $^1$H-NMR (DMSO/D$_2$O) δ=6.53 (s, 1H); 2.36 (q, 2H); 1.07 (t, 3H).

EXAMPLE 18

1-[4-(Amidino)-2,3-dihydro-1H-inden-1-ylideneamino]-2-amino-4-ethyl-imidazole dihydrochloride Analogously to Example 2, approximately 0.4 g of Raney nickel is added to a solution of 1.0 g (0.0027 mol) of 1-[4-(N-hydroxyamidino)-2,3-dihydro-11H-inden-1-ylideneamino]-2-amino-4-ethyl-imidazole dihydrochloride in 100 ml of methanol, and hydrogenation is carried out at room temperature and under normal pressure until the absorption of hydrogen has ceased. The reaction mixture is then filtered, adjusted to pH 4 with a small amount of 2N alcoholic hydrochloric acid and concentrated to dryness by evaporation. The residue is recrystallized from ethanol, yielding the title compound in the form of the dihydrate, m.p. >240° C. (decomp.), $^1$H-NMR (DMSO/D$_2$O): δ=8.21 (d, 1H); 7.75 (d, 1H); 7.6 (t, 1H); 7.18 (s, 1H); 3.26 (m, 2H); 3.18 (m, 2H); 2.46 (q. 2H): 1.15 (t, 3H).

EXAMPLE 19

1-[4-(N-Hydroxyamidino)-2,3-dihydro- 1H-inden-1-ylideneamino]-2-amino-4,5-dihydro-imidazole dihydrochloride 0.5 ml of 32% hydrochloric acid (Merck, Darmstadt, Germany; p.a.) is added, with stirring, to a mixture of 0.51 g (0.0025 mol) of 4-(N-hydroxyamidino)-2,3-dihydro-1H-inden-1-one oxime, 0.342 g (0.0025 mol) of 1,2-diamino-4,5-dihydro-imidazole hydrochloride [m.p. 245°–246° C.; prepared from the corresponding p-toluenesulfonate salt, see EP 0 327 919, Example 12, by ion exchange on ®Amberlite IRA-400 (anion exchanger based on a styrene/divinylbenzene polymer with quaternary ammonium groups in the Cl$^-$ form; Fluka, Buchs, Switzerland)] and 12 ml of isopropanol, and the reaction mixture is stirred at 80°–90° C. for 16 hours. The reaction mixture is filtered while hot and the filtration product is washed with isopropanol and recrystallized from hot water. In that manner there is obtained the title compound, m.p. >245° C., $^1$H-NMR (D$_2$O): δ=8.08 (d, 1H); 7.72 (d, 1H); 7.56 (t, 1H); 4.14 (t, 2H); 3.81 (t, 2H); 3.3 (m, 2H); 3.15 (m, 2H).

EXAMPLE 20

1-[4-(Amidino)-2,3-dihydro-1H-inden-1-ylideneamino]-2-amino-4,5-di-hydro-imidazole dihydrochloride Analogously to Example 2, approximately 2.0 g of Raney nickel are added to a solution of 4.75 g (0.0138 mol) of 1-[4-(N-hydroxyamidino)-2,3-dihydro-1H-inden-1-ylideneamino]-2-amino-4,5-dihydro-imidazole dihydrochloride in 240 ml of water, and hydrogenation is carried out at room temperature and under normal pressure until the absorption of hydrogen has ceased. The reaction mixture is then filtered, adjusted to pH 4 with a small amount of 2N alcoholic hydrochloric acid and concentrated to dryness by evaporation. The residue is recrystallized from water, yielding the title compound in the form of the monohydrate, m.p. 280° C. (decomp.), $^1$H-NMR (DMSO/D$_2$O): δ=8.17 (d, 1H); 7.66 (d, 1H); 7.54 (t, 1H); 4.18 (t, 2H); 3.70 (t, 2H); 3.25 (m, 2H); 3.13 (m, 2H).

EXAMPLE 21

1-[4-(N-Hydroxyamidino)-2,3-dihydro-1H-inden-1-ylideneamino]-2-amino-4-(4-biphenylyl)-imidazole dihydrochloride 20 ml of concentrated hydrochloric acid are added, with stirring, to a mixture of 5.09 g (0.0248 mol) of 4-(N-hydroxyamidino)-2,3-dihydro-1H-inden-1-one oxime, 6.23 g (0.0248 mol) of 1,2-diamino-4-(4-biphenylyl)-imidazole and 70 ml of isopropanol, and the mixture is stirred at 120° C. for 28 hours. Cooling to room temperature, filtration, washing the crystallizate with isopropanol and drying under a high vacuum yield the title compound with a water content of 0.9%, m.p. 284°–285° C. (decomp.), $^1$H-NMR (DMSO/D$_2$O): δ=8.28 (d, 1H); 7.99 (s, 4H); 7.80 (s, 4H); 7.60–7.76 (m, 4H); 7.35–7.53 (m, 3H); 3.32 (s, 4H).

The starting materials are prepared as follows:

a) 2-Amino-1-benzylideneamino-4-(4-biphenylyl)-imidazole 7 ml (0.0507 mol) of triethylamine and 13.75 g (0.050 mol) of 2-bromo-4'-phenylaceto-phenone (Aldrich, Buchs, Switzerland; tech., Cat. no. 10,108-7) are added to a solution of 8.11 g (0.05 mol) of benzaldehyde guanylhydrazone in 40 ml of ethanol. The reaction mixture is stirred at 20° C. for 15 hours and is filtered, and the crystallizate is taken up in methylene chloride and acidified to pH 1 with 1N hydrochloric acid. After filtration, the filtration product is taken up in methanol, and 2N sodium hydroxide solution is added until a basic reaction is obtained (pH 11). Filtration is carried out and the crystalline product is washed with methanol/water (1:1). The title compound so obtained melts at 254°–255° C. (decomp.), $^1$H-NMR (DMSO): δ=8.60 (s, 1H); 8.10 (s, 1H); 7.93–7.98 (m, 2H); 7.67–7.83 (m, 6H); 7.32–7.55 (m, 6H); 6.24 (s, 2H).

b) 1,2-Diamino-4-(4-biphenylyl)-imidazole

A solution of 9.2 g (0.0189 mol) of 2-amino-1-benzylideneamino-4-(4-biphenylyl)-imidazole and 22 ml of hydrazine hydrate in 73 ml of diethylene glycol is stirred at 140° C. for 48 hours. After cooling to 20° C., 100 ml of acetonitrile are added to the reaction mixture, which is then cooled further to 5° C. The product that has separated out is filtered off and washed with acetonitrile and diethyl ether. In that manner there is obtained the title compound having a water content of 0.41 %, m.p. >280° C., $^1$H-NMR (DMSO): δ=7.29–7.73 (m, 9H); 7.12 (s, 1H); 5.55 (s, 2H); 5.39 (s, 2H).

EXAMPLE 22

1-[4-(Amidino)-2,3-dihydro-1H-inden-1-ylideneamino]-2-amino-4-(4-bi-phenylyl)-imidazole dihydrochloride Analogously to Example 2, a mixture of 9.27 g (18.54 mmol) of 1-[4-(N-hydroxy-amidino)-2,3-dihydro-1H-inden-1-ylideneamino]-2-amino-4-(4-biphenylyl)-imidazole dihydrochloride, 800 ml of water, 820 ml of methanol and 7.3 g of Raney nickel is hydrogenated at 25°–51° C. and under normal pressure until the absorption of hydrogen has ceased. The reaction mixture is then filtered, the filtrate is acidified to pH 1 with concentrated hydrochloric acid, and concentration is carried out by evaporation in vacuo. Recrystallization of the residue twice from ethanol yields the title compound, m.p. 269°–270° C. (decomp.), $^1$H-NMR (DMSO/D$_2$O): δ=8.32 (d, 1H); 8.03 (s, 1H); 7.62–7.83 (m, 8H); 7.35–7.53 (m, 3H); 3.36 (s, 4H).

EXAMPLE 23

1-[4-(N-Hydroxyamidino)-2,3-dihydro-1H-inden-1-ylideneamino]-2-amino-4-(2-naphthyl)-imidazole dihydrochloride 7 ml of concentrated hydrochloric acid are added, with stirring, to a mixture of 2.01 g (9.8 mmol) of 4-(N-hydroxyarnidino)-2,3-dihydro-1H-inden-1-one oxime, 2.2 g (9.8 mmol) of 1,2-diamino-4-(2-naphthyl)-imidazole (see J. Heterocycl. Chem. 11, 327–329 (1974)) and 25 ml of isopropanol, and the mixture is stirred at 120° C. for 24 hours. The mixture is cooled to 20° C., filtered and washed with isopropanol, and the filtration product is taken up in 60 ml of methylene chloride. The suspension is stirred at room temperature for 15 hours and is then filtered, and the crystallizate is washed with methylene chloride. In that manner there is obtained the title compound, m.p. 265°–270° C., $^1$H-NMR (DMSO/D$_2$O): δ=8.32 (s, 1H); 8.29 (d, 1H); 8.19 (s, 1H); 8.04 (d, 1H); 7.88–7.98 (m, 3H); 7.81 (d, 1H); 7.53–7.68 (m, 3H); 3.38 (s, 4H).

EXAMPLE 24

1-[4-(Amidino)-2,3-dihydro-1H-inden-1-ylideneamino]-2-amino-4-(2-naphthyl)-imidazole dihydrochloride Analogously to Example 2, 0.3 g of Raney nickel is added to a mixture of 1.0 g (2.13 mmol) of 1-[4-(N-hydroxyamidino)-2,3-dihydro-1H-inden-1-ylideneamino]-2-amino-4-(2-naphthyl)-imidazole dihydrochloride in 120 ml of methanol/water (1:1), and hydrogenation is carried out at room temperature and under normal pressure until the absorption of hydrogen has ceased. The reaction mixture is then filtered, the filtrate is acidified to pH 3 with 3N methanolic hydrochloric acid, and concentration is carried out by evaporation in vacuo. Recrystallization of the residue from ethanol with the addition of a small amount of methanol yields the title compound, m.p. >280° C., $^1$H-NMR (DMSO/D$_2$O): δ=8.31 (d, 1H); 8.18 (s, 1H); 8.05 (s, 1H); 7.92–8.03 (m, 3H); 7.79–7.86 (m, 2H); 7.52–7.69 (m, 3H); 3.35 (s, 4H).

EXAMPLE 25

1-[4-(N-Hydroxyamidino)-2,3-dihydro-1H-inden-1-ylideneamino]-2-amino-imidazole dihydrochloride A mixture of 0.837 g (4.079 mmol) of 4-(N-hydroxyamidino)-2,3-dihydro-1H-inden-1-one oxime, 0.40 g (4.077 mmol) of 1,2-diamino-imidazole, 23 ml of isopropanol and 1.33 ml of concentrated hydrochloric acid is heated under reflux for 22 hours. Filtration of the hot reaction mixture, washing of the crystallizate with isopropanol and diethyl ether and drying under a high vacuum yield the title compound, m.p. 258°–260° C. (decomp.), $^1$H-NMR (DMSO/D$_2$O): δ=8.29 (d, 1H); 7.80 (d, 1H); 7.65 (t, 1H); 7.55 (d, 1H); 7.13 (d, 1H); 3.22–3.32 (m 4H).

The starting materials are prepared as follows:

a) N-Benzylidenamino-N'-(2,2-dimethoxy-ethyl)-guanidine 2.88 g (0.06 mol) of sodium hydride dispersion (approximately 50% in oil; Fluka, Buchs, Switzerland) are added in portions over a period of 10 minutes, with stirring and with the introduction of nitrogen, to a solution of 8.1 g (0.05 mol) of benzaldehyde guanylhydrazone in 80 ml of DMF. After 25 minutes stirring at room temperature, 7.1 ml (0.06 mol) of bromoacetaldehyde dimethylacetal (Aldrich, Buchs, Switzerland; 97%, Cat. no. 24,250-0) are added dropwise to the mixture, which has been cooled in an ice-bath. The reaction mixture is stirred for one hour at room temperature and for 20 hours at 55° C., and then concentration by evaporation is carried out in vacuo and the residue is partitioned between ethyl acetate and water. The organic phase is washed with water and brine and is concentrated by evaporation, and the oily residue is purified by flash chromatography on silica gel having a particle size of 0.04–0.063 mm, using ethyl acetate and ethyl acetate/methanol (9:1). Concentration of the product-containing fractions by evaporation yields the title compound in the form of an oil, Rf value=0.80 (silica gel/methylene chloride:methanol:conc. ammonia (40:10:1)), $^1$H-NMR (DMSO): δ=8.07 (s, 1H); 7.67–7.73 (m, 2H); 7.23–7.40 (m, 3H); 5.93 (bs, 3H); 4.48 (t, 1H); 3.32 (s, 6H); 3.29 (d, 2H).

b) 1,2-Diamino-imidazole

A mixture of 2.5 g (0.01 mol) of N-benzylideneamino-N'-(2,2-dimethoxyethyl)guanidine and 50 ml of 2N hydrochloric acid is heated slowly from 60° C. to 120° C. over a period of 4 hours, with stirring. The benzaldehyde that is separated off during the course of the reaction is removed from the reaction mixture by azeotropic distillation (approximately 2 hours). After making up to the original volume by the addition of water, the reaction mixture is heated for a further 8 hours under reflux and is then concentrated by evaporation in vacuo. The resinous residue is dissolved in a mixture of 3 ml of methanol and 2.5 ml of 30% sodium hydroxide solution and is purified by flash chromatography on silica gel having a particle size of 0.04–0.063 mm using methylene chloride:methanol (9:1) and methylene chloride:methanol:conc. ammonia (90:10:0.5 and 40:10:1). Concentration of the product-containing fractions by evaporation yields the title compound in the form of an oil, $^1$H-NMR (DMSO): δ=6.60 (s, 1H); 6.38 (s, 1H); 5.67 (bs, 2H); 5.54 (bs 2H).

EXAMPLE 26

1-[4-(Amidino)-2,3-dihydro-1H-inden-1-ylideneamino]-2-amino-imidazole dihydrochloride 0.3 g of Raney nickel is added to a solution of 0.8 g (2.33 mmol) of 1-[4-(N-hydroxy-amidino)-2,3-dihydro-1H-inden-1-ylideneamino]-2-amino-imidazole dihydrochloride in 60 ml of methanol/water (1:1), and hydrogenation is carried out at room temperature and under normal pressure until the absorption of hydrogen has ceased. The filtrate is adjusted to pH 3 with a small amount of 3N methanolic hydrochloric acid and is concentrated by evaporation in vacuo. Recrystallization of the residue from methanol/water yields the title compound, m.p. >260° C., $^1$H-NMR (D$_2$O): δ=8.15 (d, 1H); 7.82 (d, 1H); 7.58 (t, 1H); 7.17 (d, 1H); 6.90 (d, 1H); 3.29–3.35 (m, 2H); 3.12–3.18 (m, 2H).

EXAMPLE 27

1-[4-(N-HydroxVamidino)-213-dihydro-1H-inden-1-ylideneamino]-2-amino-4-(4-tert-butylphenyl)-imidazole dihydrochloride 0.45 ml of 32% hydrochloric acid (Merck, Darmstadt, Germany; p.a.) is added, with stirring, to a mixture of 0.307 g (0.0015 mol) of 4-(N-hydroxyamidino)-2,3-dihydro-1H-inden-1-one oxime, 0.345 g (0.0015 mol) of 1,2-diamino-4-(4-tert-butylphenyl)-imidazole (see Ivaschenko A. V. et aL, Khim. Geterotsikl. Soedin. (2), 236–241 (1982)—English translation: Chem. Heterocycl. Compd. 1982, 185–189) and 7.5 ml of isopropanol, and the reaction mixture is stirred at 80°–90° C. for 16 hours. The reaction mixture is filtered while hot and the filtration product is washed with isopropanol and dried. In that manner there is obtained the title compound, m.p. >250° C., $^1$H-NMR (D$_2$O): δ=8.26 (d, 1H); 7.86 (s, 1H); 7.75 (d, 1H); 7.6 (m, 3H); 7.47 (d, 2H); 3.28 (s, 4H); 1.27 (s, 9H).

EXAMPLE 28

1-[4-(Amidino)-2,3-dihydro- 1H-inden-1-ylideneaminol-2-amino-4-(4-tert-butylphenyl)-imidazole dihydrochloride Analogously to Example 2, approximately 2.0 g of Raney nickel are added to a solution of 3.9 g (0.0082 mol) of 1-[4-(N-hydroxyamidino)-2,3-dihydro-1H-inden-1-ylideneamino]-2-amino-4-(4-tert-butylphenyl)-imidazole dihydrochloride in 400 ml of methanol, and hydrogenation is carried out at room temperature and under normal pressure until the absorption of hydrogen has ceased. The reaction mixture is then filtered, adjusted to pH 4 with a small amount of 2N alcoholic hydrochloric acid and concentrated to dryness by evaporation. The residue is recrystallized from ethanol, yielding the title compound in the form of the trihydrate, m.p. 250° C. (decomp.), $^1$H-NMR (DMSO/D$_2$O): δ=8.27 (d, 1H); 7.75–7.92 (m, 2H); 7.6 (m, 3H); 7.46 (m, 2H); 3.32 (bs, 4H); 1.27 (s, 9H).

EXAMPLE 29

1-[4-(Amidino)-2,3-dihydro-1H-inden-1-ylideneamino]-2-amino-4,5-di-hydro-imidazole dihydrochloride A solution of 0.24 g (0.001 mol) of 4-amidino-2,3-dihydro-1H-inden-1-one hydrochloride and 0.136 g (0.001 mol) of 1,2-diamino-4,5-dihydro-imidazole hydrochloride [m.p. 245°–246° C., prepared from the corresponding p-toluenesulfonate salt, see EP 0 327 919, Example 12, by ion exchange on ®Amberlite IRA-400 (anion exchanger based on a styrene/divinylbenzene polymer with quaternary ammonium groups in the Cl$^-$ form; Fluka, Buchs, Switzerland)] in 3 ml of water is left to stand at room temperature for 18 hours. The product that has crystallized out is filtered off with suction and recrystallized from water, yielding the title compound (monohydrate), m.p. 280° C. (decomp.), $^1$H-NMR (DMSO/D$_2$O): δ=8.17 (d, 1H); 7.66 (d, 1H); 7.54 (t, 1H); 4.18 (t, 2H); 3.70 (t, 2H); 3.25 (m, 2H); 3.13 (m, 2H).

The starting materials are prepared as follows:
a) 4-Thiocarbamoyl-2,3-dihydro-1H-inden-1-one A solution of 12.1 g (77 mmol) of 4-cyano-2,3-dihydro-1H-inden-1-one [see Coll. Czechoslov. Chem. Commun. 4, 3227 (1978)] in 220 ml of pyridine and 10.6 ml (77 mmol) of triethylamine is saturated with hydrogen sulfide for 3 hours at 40° and is then stirred at the same temperature for 16 hours. The reaction mixture is cooled and then concentrated to dryness by evaporation, and 300 ml of water are added to the residue. The yellow product that has crystallized out is filtered off with suction, washed with water, dried and recrystallized from ethyl acetate. In that manner there is obtained the title compound, m.p. 197° (decomp.).

b) 4-Amidino-2,3-dihydro-1H-inden-1-one hydrochloride 10.8 g (54 mmol) of triethyloxonium tetrafluoroborate are added at room temperature, under argon, to a solution of 9.8 g (51.3 mmol) of 4-thiocarbamoyl-2,3-dihydro-1H-inden-1-one in 500 ml of absolute methylene chloride. After 16 hours, a mixture of 4.2 g of potassium carbonate and 4.2 ml of water is added to the reaction solution. The mixture is then stirred briefly and is filtered, and the filtrate is washed with water. The organic phase is dried over magnesium sulfate, filtered and concentrated by evaporation. The crude ethylthio-imino ether so obtained is dissolved in 160 ml of absolute ethanol; 3.3 g (60 mmol) of ammonium chloride are added and the reaction mixture is heated at reflux for 20 hours. After cooling, the reaction mixture is concentrated to dryness by evaporation. The title compound is purified by chromatography on 1000 ml of ®Amberlite ER-180 (Rohm & Haas, Darmstadt, Germany; ER-180 is a polystyrene-based adsorbate resin which is used for separating off lipophilic impurities and for decoloring; water as eluant) and is recrystallized from ethanol/diethyl ether, m.p. 215°–218° (decomp.).

EXAMPLE 30

1-[5-(Amidino)-tetralin-1-ylideneamino]-2-amino-4,5-dihydro-imidazole dihydrochloride 0.2 ml of 32% hydrochloric acid (Merck, Darmstadt, Germany; p.a.) is added, with stirring, to a solution of 0.25 g (0.001 mol) of 5-(amidino)-1-tetralone hydrochloride and 0.136 g (0.001 mol) of 1,2-diamino-4,5-dihydro-imidazole hydrochloride in 5 ml of iso-propanol, and the mixture is stirred at 80°–90° C. for 16 hours. The reaction mixture is filtered while hot and the filtration product is washed with isopropanol and dried, yielding the title compound, m.p. >220° C. (decomp.), $^1$H-NMR (DMSO/D$_2$O): δ=8.15 (d, 1H); 7.67 (d, 1H); 7.55 (t, 1H); 4.17 (t, 2H); 3.68 (t, 2H); 3.23 (m, 2H); 3.15 (m, 2H); 1.9 (m, 2H).

The starting materials are prepared as follows:
a) 5-Cyano-1-tetralone 0.41 g (4.5 mmol) of copper(I) cyanide is added to a solution of 1.0 g (4.4 mmol) of 5-bromo-1-tetralone [see J. Org. Chem. 49, 4226 (1984)] in 1.3 ml of DMF, and the reaction mixture is stirred at 160° for 6 hours. The reaction mixture is then cooled to 80°, and a solution of 1.6 g of iron(III) chloride hexahydrate in 2.5 ml of water and 0.44 ml of concentrated hydrochloric acid is added. Stirring is continued for 45 minutes, the reaction mixture is cooled and diluted with water, and extraction is carried out with toluene. The organic phase is washed with water, dried over magnesium sulfate, filtered and concentrated by evaporation. In that manner there is obtained the title compound in the form of yellow-orange crystals, IR (CH$_2$Cl$_2$): 2220, 1690 cm$^{-1}$; $^1$H-NMR (CDCl$_3$): δ=8.26 (q,1H); 7.81 (q,1H); 7.43 (t,1H); 3.21 (t,2H); 2.72 (t,2H); 2.23 (m,2H).

b) 5-Thiocarbamoyl-1-tetralone

Analogously to Example 29a), 10.6 g (62 mmol) of 5-cyano-l-tetralone in 200 ml of pyridine and 8.6 ml of triethylamine are treated with hydrogen sulfide and worked up. There is thus obtained the title compound in the form of yellow crystals, m.p. 200°–205°.

c) 5-Amidino-1-tetralone hydrochloride

Analogously to Example 29b), 8.6 g (42 mmol) of 5-thiocarbamoyl-1-tetralone are treated with 8.8 g (44 mmol) of triethyloxonium tetrafluoroborate and 2.6 g (49 mmol) of ammonium chloride. There is thus obtained the title compound in the form of slightly pink-colored crystals, MS (FAB): (M+H)$^+$=189.

EXAMPLE 31

1-[5-(Amidino)-tetralin-1-ylideneamino]-2-amino-4-phenyl-imidazole di-hydrochloride Analogously to Example 3, 5-(amnidino)-1-tetralone hydrochloride is reacted with 1,2-di-amino-4-phenyl-imidazole, yielding the title compound. M.p. >240° C. (decomp.), $^1$H-NMR (DMSO/D$_2$O) δ=8.54 (d, 1H); 7.6–7.8 (m, 4H); 7.3–7.58 (M, 5H); 2.96 (m, 2H); 2.88 (m, 2H); 1.9 (m, 2H).

EXAMPLE 32

1-[4-(N-Hydroxyamidino)-2,3-dihydro-1H-inden-1-ylideneamino]-2-amino-4-phenyl-imidazole dihydrochloride A mixture of 0.406 g (0.0019 mol) of 4-cyano-2,3-dihydro-1H-inden-1-one 2'-amidino-hydrazone (prepared from the HCl salt in aqueous solution with NaOH) and 0.19 g (0.0009 mol) of phenacyl bromide (Aldrich, Buchs, Switzerland; Cat. No. 11,583-5) in 40 ml of ethanol is boiled under reflux for 4 hours. The reaction mixture is filtered while hot and the filtration product is washed with ethanol and dried, yielding 1-[4-cyano-2,3-di-hydro-1H-inden-1-ylideneamino]-2-amino-4-phenyl-imidazole, MS (FAB): (M+H)$^+$=314, $^1$H-NMR (DMSO): δ=8.32 (d, 1H); 7.94 (d, 1H); 7.76 (m, 3H); 7.56 (t, 1H); 7.32 (m, 2H); 7.16 (t, 1H); 6.12 (s, 2H); 3.35 (bs, 4H).

That intermediate is maintained under reflux in ethanol for 4 hours with equivalent amounts of hydroxylamine hydrochloride and sodium carbonate, the title compound being obtained after working up with hydrochloric acid (for physical data see Example 1).

The starting material is prepared as follows:

a) 4-Cyano-2,3-dihydro-1H-inden-1-one 2-amidinohydrazone hydrochloride 314 mg (2 mmol) of 4-cyano-2,3-dihydro-1H-inden-1-one are dissolved in 20 ml of methanol, a solution of 272 mg (2 mmol) of aminoguanidine hydrogen carbonate in 9 ml of water and 1 ml of 2N hydrochloric acid are added thereto and the mixture is stirred at reflux for 4 days. After cooling, the reaction mixture is concentrated to dryness by evaporation and the residue is crystallized from water. There is thus obtained the title compound, m.p. >230° C.; $^1$H-NMR (DMSO-d$_6$/D$_2$O): δ=8.16 (d,1H); 7.9 (d,1H); 7.55 (t,1H); 3.28 (m,2H); 2.9 (m,2H); IR(Nujol): 2190 cm$^{-1}$ (CN).

EXAMPLE 33

1-(3-Amidinobenzylideneamino)-2-amino-4-phenyl-imidazole dihydrochloride

Analogously to Example 31, 3-amidinobenzaldehyde hydrochloride is reacted with 1,2-di-amino-4-phenyl-imidazole, yielding the title compound.

The starting material is prepared as follows:

a) Ethyl-3-formylbenzimidate hydrochloride (3-formyl-benzimide acid ethyl ester chloride):

59.7 ml (1.025 mol) of absolute ethanol are added to a solution of 86.7 g (0.662 mol) of 3-cyanobenzaldehyde (Aldrich, Buchs, Switzerland, Cat. No. 14,625-0) in 530 ml of absolute diethyl ether and the reaction solution is cooled to 0° C. The reaction solution is saturated with dry hydrochloric acid gas and then left to stand at 0° C. for 6 days. When a fine precipitate has been filtered off, 1 liter of diethyl ether is added to the reaction solution. The title compound crystallizes out, m.p. 126°–128° C. (with foaming).

b) 3-Amidinobenzaldehyde hydrochloride 250 ml of absolute ethanol and 250 ml of saturated ethanolic ammonia solution are added to 21.3 g (0.1 mol) of the imino ether from Example 33a) and the mixture is heated at 70° C. for 3 hours. After cooling, the ethanol is evaporated off and the residue, which corresponds to the title compound in crude form, is reacted further directly.

EXAMPLE 34

1-(α-Methyl-3-amidinobenzylideneamino)-2-amino-4-phenyl-imidazole di-hydrochloride Analogously to Example 3, 3-amidinoacetophenone hydrochloride is reacted with 1,2-di-amino-4-phenyl-imidazole, yielding the title compound.

The starting material is prepared as follows:

a) Ethyl-3-acetylbenzimidate hydrochloride (3-acetyl-benzimide acid ethyl ester hydrochloride)

A solution of 7.25 g (0.05 mol) of 3-acetylbenzonitrile (Aldrich, Buchs, Switzerland; Cat. No. 29,221-4) in 150 ml of diethyl ether and 4.5 ml of ethanol is saturated at 0° C. with dry hydrochloric acid gas and then left to stand at 0° C. for 2 days. The product that has crystallized out is filtered off and the title compound is obtained after recrystallization from ethanol/diethyl ether, m.p. 110° C. (decomp.).

b) 3-Amidinoacetophenone hydrochloride 11.4 g of the title compound from Example 34a), 200 ml of ethanol and 125 ml of saturated ethanolic ammonia solution are boiled at reflux for 6 hours. After cooling, the reaction mixture is concentrated by evaporation, and the residue is dissolved in 4N hydrochloric acid, washed with diethyl ether and concentrated to dryness by evaporation. The resulting crude product (title compound) is used further directly.

The following compounds are prepared analogously to one of the methods described in this Application (Examples 35 to 44)

EXAMPLE 35

1-[4-(Amidino)-2,3-dihydro-1H-inden-1-ylideneamino]-2-amino-4-(3,4-di-methoxyphenyl)-imidazole dihydrochloride

EXAMPLE 36

1-[4-(Amidino)-2,3-dihydro-1H-inden-1-ylideneamino]-2-amino-4-(3,4,5-tri-methoxyphenyl)-imidazole dihydrochloride

EXAMPLE 37

1-[4-(Amidino)-2,3-dihydro-1H-inden-1-ylideneamino]-2-amino-4-(3,5-di-methoxyphenyl)-imidazole dihydrochloride

EXAMPLE 38

1-[4-(Amidino)-2,3-dihydro-1H-inden-1-ylideneamino]-2-amino-4-(3,4-di-methylphenyl)-imidazole dihydrochloride

EXAMPLE 39

1-[4-(Amidino)-2,3-dihydro-1H-inden-1-ylideneamino]-2-amino-4-(3,5-di-methylphenyl)-imidazole dihydrochloride

EXAMPLE 40

1-[4-(Amidino)-2,3-dihydro-1H-inden-1-ylideneamino]-2-amino-4-(2,4-di-methylphenyl)-imidazole dihydrochloride

EXAMPLE 41

1-[4-(Amidino)-2,3-dihydro-1H-inden-1-ylideneamino]-2-amino-4-(3,4-di-chlorophenyl)-imidazole dihydrochloride

EXAMPLE 42

1-[4-(Amidino)-2,3-dihydro-1H-inden-1-ylideneamino]-2-amino-4-(3,5-di-chlorophenyl)-imidazole dihydrochloride

EXAMPLE 43

1-[4-(Amidino)-2,3-dihydro-1H-inden-1-ylideneamino]-2-amino-4-(2,4-di-chlorophenyl)-imidazole dihydrochloride

EXAMPLE 44

1-14-(Amidino)-2,3-dihydro-1H-inden-1-ylideneamino]-2-amino-4-(3,5-di-(tert-butyl)phenyl)-imidazole dihydrochloride

EXAMPLE 45

Capsules

Capsules containing 1 g of active ingredient, i.e. a compound of formula I according to any one of Examples 1 to 34, are prepared as follows:

| Composition (for 1250 capsules): | |
|---|---|
| active ingredient | 1250 g |
| talc | 180 g |
| wheat starch | 120 g |
| magnesium stearate | 80 g |
| lactose | 20 g |

The pulverulent substances are forced through a sieve of 0.6 mm mesh size and mixed. 1.32 g portions of the mixture are introduced into gelatin capsules using a capsule-filling machine.

EXAMPLE 46

Tablets 10000 tablets, each comprising 5 mg of active ingredient, i.e. one of the compounds of formula I prepared in Examples 1 to 34, are prepared:

| Composition: | |
|---|---|
| active ingredient | 50.00 g |
| lactose | 2535.00 g |
| corn starch | 125.00 g |
| polyethylene glycol 6.000 | 150.00 g |
| magnesium stearate | 40.00 g |
| purified water | quantum satis |

Method: All the pulverulent constituents are forced through a sieve of 0.6 mm mesh size. Then the active ingredient, the lactose, the magnesium stearate and half the starch are mixed in a suitable mixer. The other half of the starch is suspended in 65 ml of water and the resulting suspension is added to a boiling solution of the polyethylene glycol in 260 ml of water. The paste that is formed is added to the powder mixture and granulated, if necessary with the addition of more water. The granules are dried overnight at 35° C., forced through a sieve of 1.2 mm mesh size and compressed to form tablets having a breaking notch.

EXAMPLE 47

Infusion or injection solutions

Infusion or injection solutions comprising 100 mg of active ingredient dissolved in 5 ml of aqueous 5% D-glucose solution are prepared. The active ingredient used is one of the compounds from Examples 1 to 34. The solutions are introduced into vials.

EXAMPLE 48

Dry vials

Dry vials are parepared by lyophilising solutions prepared in Example 37 of one of the active ingredients mentioned therein.

EXAMPLE 49

Inhibition of S-adenosylmethionine decarboxylase (SAMDC)

Using the method of A. E. Pegg and H. S. Pöso (see Methods Enzymol. 94, 234–239 (1983)) mentioned hereinbefore, the following $IC_{50}$ values are obtained for the inhibition of the enzyme SAMDC for the compounds of formula I mentioned below:

| Title compound of formula I from Example | $IC_{50}$ (mM) |
|---|---|
| 2 | 2 |
| 4 | 3.6 |
| 6 | 8.4 |
| 8 | 8.9 |
| 10 | 4.2 |
| 12 | 6.7 |
| 14 | 3.4 |
| 16 | 4.0 |
| 18 | 6.1 |
| 20 | 3.4 |
| 22 | 11 |
| 24 | 7.5 |
| 28 | 5.4 |

EXAMPLE 50

Inhibition of the growth of human T24 bladder carcinoma cells:

The inhibition of the growth of human T24 bladder carcinoma cells is measured using the method mentioned hereinbefore. The following $IC_{50}$ values (concentration of the test compound at half the maximum inhibition) are determined using the following Examples:

| Title compound of formula I from Example | $IC_{50}$ (mM) |
|---|---|
| 2 | 1.16 |
| 4 | 2 |
| 6 | 1.2 |
| 8 | 1.6 |
| 10 | 2.6 |
| 12 | 1.55 |
| 14 | 1.12 |
| 16 | 2.70 |
| 18 | 1.5 |
| 20 | 0.28 |
| 22 | 0.44 |
| 24 | 2.46 |
| 26 | 2.15 |
| 28 | 0.23 |

EXAMPLE 51

Inhibition of the growth of T24 bladder carcinoma cells in vivo (nude mouse)

Using the method mentioned hereinbefore (see also Regenass et al., Cancer Res. 54, 3210–3217 (1974)), the compound of Example 2 of the present Application is administered in accordance with the following treatment scheme to BALB/c nude mice with transplanted human T24 bladder cell carcinomas: The compound is administered p.o. (50, 25 and 12.5 mg/kg) or i.p. (12.5, 6.25 and 3.13 mg/kg). The compound is dissolved in distilled water and diluted with 3 volumes of 0.9% NaCl (w/v) in water.

As shown in the following Table, 1-[4-(amidino)-2,3-dihydro-1H-inden-1-ylideneamino]-2-amino-4-phenyl-imidazole dihydrochloride inhibits the growth of T24 bladder carcinoma cells both on oral and on intraperitoneal administration. The dose-dependence of the action is observed. The maximum tolerated dose is >500 mg/kg in the case of p.o. administration and 125 mg/kg in the case of i.p. administration.

Inhibition of T24 tumor growth:

| Title compound from Example 2 | T/C (%)* on administration | |
| --- | --- | --- |
| (mg/kg) | i.p. | p.o. |
| 0 (control) | 100 | 100 |
| 3.13 | 34 | n.d. |
| 6.25 | 22 | n.d. |
| 12.5 | 16 | 68 |
| 25 | n.d. | 47 |
| 50 | n.d. | 31 |

(n.d. = not determined)
*average for 6 animals

What is claimed is:
1. A compound of formula I

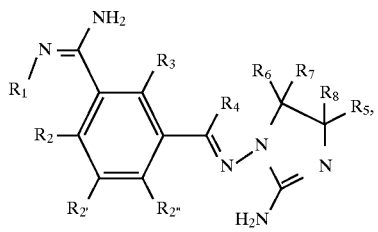

wherein
$R_1$ is hydroxy or hydrogen;
the radicals $R_2$, $R_2'$ and $R_2''$ are each independently of the others hydrogen or a substituent selected from lower alkyl, halo-lower alkyl having one or more halogen atoms, $C_3$–$C_8$cycloalkyl, phenyl-lower alkyl, hydroxy, lower alkoxy, phenyl-lower alkoxy, phenyloxy, lower alkanoyloxy, benzoyloxy, halogen, amino, N-lower alkylamino, N,N-di-(lower alkyl)amino, lower alkanoylamino, benzoylamino, nitro, lower alkanoyl, benzoyl, carboxy, lower alkoxycarbonyl, 1-phenyl-lower alkoxycarbonyl, carbamoyl, N-lower alkylcarbamoyl, N,N-di(lower alkyl)carbamoyl, N-phenylcarbamoyl, cyano, mercapto, lower alkylthio, lower alkanesulfonyl, sulfamoyl, N-lower alkylsulfamoyl and N,N-di (lower alkyl)sulfamoyl;
either
$R_3$ is hydrogen and
$R_4$ is hydrogen or lower alkyl,
or
$R_3$ and $R_4$ together form a divalent radical of the formula —($CH_2$)n—wherein n is 2 or 3;
$R_5$ and $R_6$ are each independently of the other hydrogen, lower alkyl; or phenyl or naphthyl each of which is unsubstituted or mono- to tri-substituted, wherein the substituents are selected independently of one another from the group consisting of lower alkyl, phenyl, naphthyl, lower alkoxy, hydroxy, lower alkanoyloxy, nitro, amino, halogen, halo-lower alkyl, caboxy, lower alkoxycarbonyl, carbamoyl, N-lower alkylcarbamoyl, N,N-di(lower alkyl)carbamoyl, cyano, lower alkanoyl, phenyl- or naphthyl-carbonyl, lower alkanesulfonyl, sulfamoyl, N-lower alkylsulfamoyl and N,N-di-lower alkyl-sulfamoyl; and
either $R_7$ and $R_8$ are each hydrogen, or $R_7$ and $R_8$ together form a bond; a tautomer thereof, provided that at least one tautomerisable group is present; or a salt thereof.
2. A compound of formula I according to claim 1 wherein
$R_1$ is hydroxy or hydrogen;
the radicals $R_2$, $R_2'$ and $R_2''$ are each independently of the others hydrogen or a substituent selected from lower alkyl, halo-lower alkyl having one or more halogen atoms, $C_3$–$C_8$cycloalkyl, phenyl-lower alkyl, hydroxy, lower alkoxy, phenyl-lower alkoxy, phenyloxy, lower alkanoyloxy, benzoyloxy, halogen, amino, N-lower alkylamino, N,N-di-(lower alkyl)amino, lower alkanoylamino, benzoylamino, nitro, lower alkanoyl, benzoyl, carboxy, lower alkoxycarbonyl, 1-phenyl-lower alkoxycarbonyl, carbamoyl, N-lower alkylcarbamoyl, N,N-di(lower alkyl)carbamoyl, N-phenylcarbamoyl, cyano, mercapto, lower alkylthio, lower alkanesulfonyl, sulfamoyl, N-lower alkylsulfamoyl and N,N-di-(lower alkyl)sulfamoyl;
either
$R_3$ is hydrogen and
$R_4$ is hydrogen or lower alkyl,
or
$R_3$ and $R_4$ together form a divalent radical of the formula —($CH_2$)— wherein n is 2 or 3;
$R_5$ and $R_6$ are each independently of the other hydrogen, lower alkyl; or phenyl or naphthyl each of which is unsubstituted or mono- or di-substituted, wherein the substituents are selected independently of one another from the group consisting of lower alkyl, phenyl, naphthyl, lower alkoxy, hydroxy, lower alkanoyloxy, nitro, amino, halogen, halo-lower alkyl, carboxy, lower alkoxycarbonyl, carbamoyl, N-lower alkylcarbamoyl, N,N-di(lower alkyl)carbamoyl, cyano, lower alkanoyl, phenyl- or naphthyl-carbonyl, lower alkanesulfonyl, sulfamoyl, N-lower alkylsulfamoyl and N,N-di-lower alkyl-sulfamoyl; and
either $R_7$ and $R_8$ are each hydrogen, or $R_7$ and $R_8$ together form a bond;
a tautomer thereof, provided that at least one tautomerisable group is present; or a salt thereof.
3. A compound of formula I according to claim 1 wherein
$R_1$ is hydroxy or hydrogen;
$R_2$, $R_2'$ and $R_2''$ are each hydrogen;
either
$R_3$ is hydrogen and
$R_4$ is hydrogen or lower alkyl, or
$R_3$ and $R_4$ together are —($CH_2$)$_2$— or —($CH_2$)$_3$—;
$R_5$ is hydrogen, lower alkyl; or naphthyl or phenyl each of which is unsubstituted or substituted by one or two radicals selected from lower alkoxy, halogen, lower alkyl and phenyl;
$R_6$ is hydrogen; and
either $R_7$ and $R_8$ are each hydrogen, or $R_7$ and $R_8$ together form a bond;

a tautomer thereof, provided that at least one tautomerisable group is present; or a salt thereof.

4. A compound of formula I according to claim 1 wherein
$R_1$ is hydroxy or hydrogen;
the radicals $R_2$, $R_2'$ and $R_2''$ are each hydrogen;
either
$R_3$ is hydrogen and
$R_4$ is hydrogen or lower alkyl, or
$R_3$ and $R_4$ together are —$(CH_2)_2$— or —$(CH_2)_3$—;
$R_5$ is hydrogen, lower alkyl, phenyl, 2-, 3- or 4-lower alkoxyphenyl, 2,5-di-lower alkoxy-phenyl, 4-fluorophenyl, 4-chlorophenyl, 4-lower alkylphenyl, 4-biphenylyl, or 1- or 2-naphthyl;
$R_6$ is hydrogen; and either $R_7$ and $R_8$ are each hydrogen, or $R_7$ and $R_8$ together form a bond; or a salt thereof.

5. A compound of formula I according to claim 1 wherein
$R_1$, $R_2$, $R_2'$ and $R_2''$ are each hydrogen;
either
$R_3$ is hydrogen and
$R_4$ is hydrogen or methyl, or
$R_3$ and $R_4$ together are —$(CH_2)_2$— or —$(CH_2)_3$—;
$R_5$ is hydrogen, ethyl, phenyl, 2-, 3- or 4-methoxyphenyl, 2,5-dimethoxyphenyl, 4-fluorophenyl, 4-chlorophenyl, 4-methylphenyl, 4-biphenylyl or 2-naphthyl;
$R_6$ is hydrogen; and
either $R_7$ and $R_8$ are each hydrogen, or $R_7$ and $R_8$ together form a bond; or a salt thereof.

6. A compound of formula I according to any one of claim 1 wherein $R_1$ is hydrogen and the other radicals are as defined; a tautomer thereof, provided that at least one tautomerisable group is present, or a salt thereof.

7. A compound of formula I according to any one of claim 1 wherein $R_5$, $R_6$, $R_7$ and $R_8$ are each hydrogen and the other radicals are as defined; a tautomer thereof, provided that at least one tautomerisable group is present, or a salt thereof.

8. A compound of formula I according to any one of claim 1 wherein $R_3$ and $R_4$ together are —$(CH_2)_3$— or —$(CH_2)_2$— and the other radicals are as defined; a tautomer thereof, provided that at least one tautomerisable group is present, or a salt thereof.

9. A compound of formula I according to claim 1 wherein
$R_1$, $R_2$, $R_2'$ and $R_2''$ are each hydrogen;
$R_3$ and $R_4$ together are —$(CH_2)_2$— or —$(CH_2)_3$—;
$R_5$ is 3,4-dimethoxyphenyl, 3,4,5-trimethoxyphenyl, 3,5-dimethoxyphenyl, 3,4-dimethyl-phenyl, 3,5-dimethylphenyl, 2,4-dimethylphenyl, 3,4-dichlorophenyl, 3,5-dichlorophenyl, 2,4-dichlorophenyl or 3,5-di(tert-butyl)phenyl;
$R_6$ is hydrogen; and
$R_7$ and $R_8$ together form a bond; or a salt thereof.

10. 1-[4-(Amidino)-2,3-dihydro-1H-inden-1-ylideneamino]-2-amino-4-phenyl-imidazole of formula I according to claim 1, or a pharmaceutically acceptable salt thereof.

11. A compound of formula I according to claim 1, selected from the following compounds: 1-[4-(amidino)-2,3-dihydro-1H-inden-1-ylideneamino]-2-amino-4-(4-methoxyphenyl)-imidazole, 1-[4-(amidino)-2,3-dihydro-1H-inden-1-ylideneamino]-2-amino-4-(2-methoxyphenyl)-imidazole, 1-[4-(amidino)-2,3-dihydro-1H-inden-1-ylideneamino]-2-amino-4-(2,5-dimethoxy-phenyl)-imidazole, 1-[4-(amidino)-2,3-dihydro-1H-inden-1-ylideneamino]-2-amino-4-(3-methoxyphenyl)-imidazole, 1-[4-(amidino)-2,3-dihydro-1H-inden-1-ylideneamino]-2-amino-4-(4-chlorophenyl)-imidazole, 1-[4-(amidino)-2,3-dihydro-1H-inden-l-ylideneamino]-2-amino-4-(4-tolyl)-imidazole, 1-[4-(amidino)-2,3-dihydro-1H-inden-1-ylideneamino]-2-amino-4-(4-fluorophenyl)-imidazole, 1-[4-(amidino)-2,3-dihydro-1H-inden-1-ylideneamino]-2-amino-4-ethyl-imidazole, 1-[4-(amidino)-2,3-dihydro-1H-inden-1-ylideneamino]-2-amino-4,5-dihydro-imidazole, 1-[4-(amidino)-2,3-dihydro-1H-inden-1-ylideneamino]-2-amino-4-(4-biphenylyl)-imidazole, 1-[4-(amidino)-2,3-dihydro-1H-inden-1-ylideneamino]-2-amino-4-(2-naphthyl)-imidazole, 1-[4-(amidino)-2,3-dihydro-1H-inden-1-ylideneamino]-2-amino-imidazole, 1-[4-(amidino)-2,3-dihydro-1H-inden-1-ylideneamino]-2-amino-4-(4-tert-butyl-phenyl)-imidazole, 1-[4-(amidino)-2,3-dihydro-1H-inden-1-ylideneamino]-2-amino-4,5-dihydro-imidazole, 1-[5-(amidino)-tetralin-1-ylideneamino]-2-amino-4,5-dihydro-imidazole, 1-[5-(amidino)-tetralin-1 -ylideneamino]-2-amino-4-phenyl-imidazole, 1-(3-amidinobenzylideneamino)-2-amino-4-phenyl-imidazole and 1-(α-methvl-3-amidinobenzylideneamino)-2-amino-4-phenyl-imidazole; or a pharmaceutically acceptable salt thereof.

12. A compound of formula I according to claim 1, selected from the compounds

1-[4-(N-hydroxyamidino)-2,3-dihydro-1H-inden-1-ylideneamino]-2-amino-4-phenyl-imidazole, 1-[4-(N-hydroxyamidino)-2,3-dihydro-1H-inden-1-ylideneamino]-2-amino-4-(4-methoxy-phenyl)-imidazole, 1-[4-(N-hydroxyamidino)-2,3-dihydro-1H-inden-1-ylideneamino]-2-amino-4-(2-methoxy-phenyl)-imidazole, 1-[4-(N-hydroxyamidino)-2,3-dihydro-1H-inden-1-ylideneamino]-2-amino-4-(2,5-di-methoxyphenyl)-imidazole, 1-[4-(N-hydroxyamidino)-2,3-dihydro-1H-inden-1-ylideneamino]-2-amino-4-(3-methoxy-phenyl)-imnidazole, 1-[4-(N-hydroxyamidino)-2,3-dihydro-1H-inden-1-ylideneamino]-2-amino-4-(4-chloro-phenyl)-imidazole, 1-[4-(N-hydroxyamidino)-2,3-dihydro-1H-inden-1-ylideneamino]-2-amino-4-(4-tolyl)-imidazole, 1-[4-(N-hydroxyamidino)-2,3-dihydro-1H-inden-1-ylideneamino]-2-amino-4-(4-fluoro-phenyl)-imidazole, 1-[4-(N-hydroxyamidino)-2,3-dihydro-1H-inden-1-ylideneamino]-2-amino-4-ethyl-imidazole, 1-[4-(N-hydroxyamidino)-2,3-dihydro-1H-inden-1-ylideneamino]-2-amino-4,5-dihydro-imidazole, 1-[4-(N-hydroxyamidino)-2,3-dihydro-1H-inden-1-ylideneamino]-2-amino-4-(4-bi-phenylyl)-imidazole, 1-[4-(N-hydroxyamidino)-2,3-dihydro-1H-inden-1-ylideneamino]-2-amino-4-(2-naphthyl)-imidazole, 1-[4-(N-hydroxyamidino)-2,3-dihydro-1H-inden-1-ylideneamino]-2-amino-imidazole, 1-[4-(N-hydroxyamidino)-2,3-dihydro-1H-inden-1-ylideneamino]-2-amino-4-(4-tert-butyl-phenyl)-imidazole and 1-[4-(N-hydroxyamidino)-2,3-dihydro-1H-inden-1-ylideneamino]-2-amino-4-phenyl-imidazole; or a pharmaceutically acceptable salt thereof.

13. A compound of formula I according to claim 1, selected from the following compounds:

1-[4-(amidino)-2,3-dihydro-1H-inden-1-ylideneamino]-2-amino-4-(3,4-dimethoxyphenyl-imidazole dihydrochloride, 1-[4-(amidino)-2,3-dihydro-1H-inden-1-ylideneamino]-2-amino-4-(3,4,5-trimethoxy-phenyl-imidazole dihydrochloride, 1-[4-(amidino)-2,3-dihydro-1H-inden-1-ylideneamino]-2-amino-4-(3,5-dimethoxyphenyl-imidazole dihydrochloride, 1-[4-(amidino)-2,3-dihydro-1H-inden-1-ylideneamino]-2-amino-4-(3,4-dimethylphenyl-imidazole dihydrochloride, 1-[4-(amidino)-2,3-dihydro-1H-inden-1-ylideneamino]-2-amino-4-(3,5-dimethylphenyl-imidazole dihydrochloride, 1-[4-(amidino)-2,3-dihydro-1H-inden-1-ylideneamino]-2-amino-4-(2,4-dimethylphenyl-imidazole dihydrochloride, 1-[4-(amidino)-2,3-dihydro-1H-inden-1-ylideneamino]-2-amino-4-(3,4-dichlorophenyl-imidazole dihydrochloride, 1-[4-(amidino)-2,3-dihydro-1H-inden-1-ylideneamino]-2-amino-4-(3,5-dichlorophenyl-imidazole dihydrochloride, 1-[4-(amidino)-2,3-dihydro-1H-inden-1-ylideneamino]-2-amino-4-(2,4-dichlorophenyl-imidazole dihydrochloride and 1-[4-(amidino)-2,3-dihydro-1H-inden-1-ylideneamino]-2-amino-4-(3,5-di(tert-butyl)-phenyl-imidazole-dihydrochloride; or a pharmaceutically acceptable salt thereof.

14. A process for the preparation of a compound of formula I according to claim 1, a salt or a tautomer thereof, which process comprises a) reacting a compound of formula II

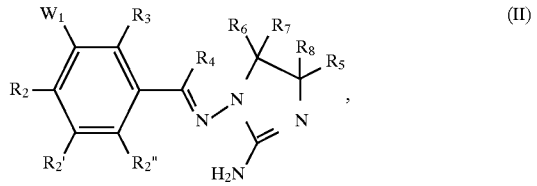

(II)

wherein $W_1$ is functionally modified carboxy and the other radicals are as defined for compounds of formula I, or a salt thereof, with hydroxyl ami-ne or ammonia of formula III

$R_1$—$NH_2$ (III), wherein $R_1$ is hydrogren or hydroxy, or with a salt thereof, functional groups in the starting materials that are not intended to participate in the reaction being, in protected form, and removing any protecting groups that are present; or b) reacting a hydroxyimino compound of formula IV

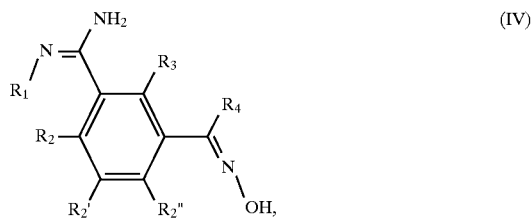

(IV)

wherein the radicals are as defined for compounds of formula I, or a salt thereof, with an aminoimidazole of formula V

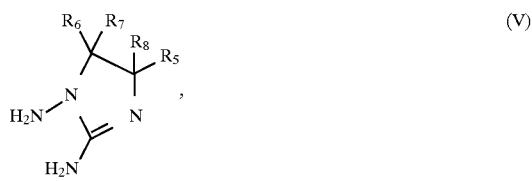

(V)

wherein the radicals are as defined for compounds of formula I, or with a salt thereof, functional groups in the starting materials that are not intended to participate in the reaction being in protected form, and removing any protecting groups that are present; or c) for the preparation of a compound of formula I wherein $R_1$ is hydrogen and the other radicals are as defined, reacting an oxo compound of formula VI

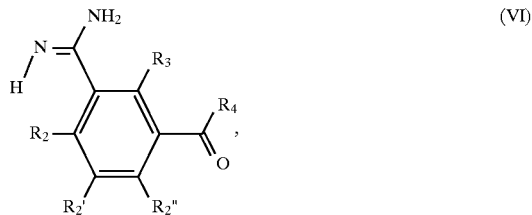

(VI)

or a reactive derivative thereof, wherein the radicals are as defined for compounds of formula I, or a salt thereof, with an amino imidazole of formula V

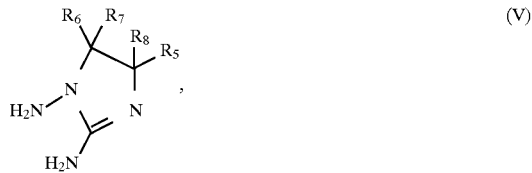

(V)

wherein the radicals are as defined for compounds of formula I, or with a salt thereof, functional groups in the starting materials that are not intended to participate in the reaction being in protected form, and removing any protecting groups that are present;

or converting a compound of formula I obtained according to one of processes a), b) or c) into a different compound of formula I converting a resulting salt of a compound of formula I into the free compound, converting into a salt a free compound of formula I having salt-forming properties that has been obtained directly or according to the last-mentioned step from a different salt, and/or, separating a resulting mixture of isomers of compounds of formula I into individual isomers.

15. A pharmaceutical composition comprising a pharmaceutically acceptable carrier or diluent and a therapeutically effective amount of a compound according to claim 1, or a pharmaceutically acceptable salt thereof.

16. A method of treating pathological conditions which are responsive to the inhibition of the enzyme S-adenosylmethionine decarboxylase comprising administering to a subject in need of such treatment a therapeutically effective amount of a compound according to claim 1, or a pharmaceutically acceptable salt thereof.

17. A method according to claim 16 for treating a proliferative disease.

18. A method according to claim 16 for treating a protozoal infection.

* * * * *